US009078647B2

(12) United States Patent
Dennison et al.

(10) Patent No.: US 9,078,647 B2
(45) Date of Patent: Jul. 14, 2015

(54) METHOD AND APPARATUS FOR DISPOSABLE GLOVE DISPENSING

(71) Applicant: No Touch Easy Gloves, Inc., Houston, TX (US)

(72) Inventors: Jack Brian Dennison, Houston, TX (US); John Owensby, Cary, NC (US); Brad Forrest, Cary, NC (US); Steve Knight, Spring, TX (US)

(73) Assignee: NO TOUCH EASY GLOVES, INC., Houston, TX (US)

( * ) Notice: Subject to any disclaimer, the term of this patent is extended or adjusted under 35 U.S.C. 154(b) by 0 days.

(21) Appl. No.: 14/332,119

(22) Filed: Jul. 15, 2014

(65) Prior Publication Data

US 2015/0053710 A1 Feb. 26, 2015

Related U.S. Application Data

(63) Continuation of application No. 14/331,061, filed on Jul. 14, 2014, now Pat. No. 8,960,493.

(60) Provisional application No. 61/870,223, filed on Aug. 26, 2013.

(51) Int. Cl.
*A41D 19/00* (2006.01)
*A61B 19/04* (2006.01)
*A47G 25/90* (2006.01)

(52) U.S. Cl.
CPC ............ *A61B 19/045* (2013.01); *A47G 25/904* (2013.01); *A61B 2019/046* (2013.01)

(58) Field of Classification Search
CPC .................................................. A41D 2400/44
USPC ............ 221/33, 45, 46, 179, 282, 283; 2/159, 2/161.6, 161.7
See application file for complete search history.

(56) References Cited

U.S. PATENT DOCUMENTS

| 3,468,100 | A | * | 9/1969 | Rubel | .............................. 53/572 |
| 4,480,750 | A | | 11/1984 | Dancy | |
| 4,537,330 | A | | 8/1985 | Gelbard | |
| 4,676,378 | A | | 6/1987 | Baxley et al. | |

(Continued)

OTHER PUBLICATIONS

USPTO; Non-Final Office Action dated Nov. 13, 2014 in U.S. Appl. No. 14/331,061.

(Continued)

*Primary Examiner* — Patrick Mackey
(74) *Attorney, Agent, or Firm* — Snell & Wilmer L.L.P.

(57) ABSTRACT

A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, where the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove. Furthermore, a disposable glove dispensing system may comprise a pack of interconnected disposable gloves, and a glove dispenser comprising two glove hangers for hanging the pack of disposable gloves hang.

24 Claims, 29 Drawing Sheets

(56) References Cited

U.S. PATENT DOCUMENTS

| | | | | |
|---|---|---|---|---|
| 4,793,539 | A | 12/1988 | Haenni et al. | |
| 4,807,754 | A | 2/1989 | Rowe | |
| 4,863,084 | A * | 9/1989 | Nabozny | 224/673 |
| 4,872,766 | A | 10/1989 | Dancy | |
| 4,911,560 | A | 3/1990 | Hoover et al. | |
| D307,555 | S | 5/1990 | Haenni et al. | |
| D308,170 | S | 5/1990 | Wilfong, Jr. | |
| 4,923,436 | A | 5/1990 | Gelbard | |
| 4,930,385 | A | 6/1990 | Wilfong, Jr. et al. | |
| RE33,264 | E * | 7/1990 | Baxley et al. | 206/554 |
| 4,942,992 | A * | 7/1990 | Fischer et al. | 224/240 |
| 4,943,167 | A | 7/1990 | Gelbard | |
| 4,953,664 | A | 9/1990 | Vrooman et al. | |
| 4,981,216 | A | 1/1991 | Wilfong, Jr. | |
| 4,995,860 | A | 2/1991 | Wilfong, Jr. | |
| 5,020,750 | A * | 6/1991 | Vrooman et al. | 248/97 |
| 5,074,674 | A | 12/1991 | Kuklies et al. | |
| D323,619 | S | 2/1992 | Wilfong, Jr. et al. | |
| D325,311 | S | 4/1992 | Mygind | |
| 5,125,604 | A | 6/1992 | Vrooman et al. | |
| 5,207,368 | A | 5/1993 | Wilfong, Jr. et al. | |
| RE34,324 | E | 7/1993 | Haenni et al. | |
| 5,323,909 | A | 6/1994 | Piraneo et al. | |
| 5,335,788 | A * | 8/1994 | Beasley et al. | 206/554 |
| 5,336,036 | A | 8/1994 | Williamson et al. | |
| 5,362,152 | A | 11/1994 | Fletcher et al. | |
| 5,421,803 | A | 6/1995 | Kemanjian | |
| 5,562,580 | A | 10/1996 | Beasley et al. | |
| 5,626,550 | A | 5/1997 | Amero et al. | |
| 5,655,682 | A * | 8/1997 | Hoffrichter | 221/45 |
| 5,667,173 | A | 9/1997 | Wilfong, Jr. et al. | |
| 5,690,229 | A | 11/1997 | Piraneo et al. | |
| D396,636 | S | 8/1998 | Wilfong, Jr. | |
| 5,806,099 | A * | 9/1998 | Grinberg | 2/158 |
| 5,845,779 | A * | 12/1998 | Wilfong et al. | 206/554 |
| 5,881,882 | A | 3/1999 | Fletcher et al. | |
| 5,924,573 | A | 7/1999 | Piraneo et al. | |
| 5,941,393 | A | 8/1999 | Wilfong, Jr. | |
| 5,966,741 | A * | 10/1999 | Klecina | 2/169 |
| 5,979,841 | A | 11/1999 | Piraneo et al. | |
| 6,142,302 | A * | 11/2000 | Requena | 206/554 |
| 6,264,035 | B1 | 7/2001 | Petrie | |
| 6,286,681 | B1 | 9/2001 | Wilfong, Jr. et al. | |
| 6,401,971 | B1 | 6/2002 | Edwards et al. | |
| 6,446,811 | B1 | 9/2002 | Wilfong, Jr. | |
| 6,497,340 | B2 * | 12/2002 | Grinberg | 221/45 |
| 6,578,729 | B2 * | 6/2003 | Grinberg | 221/26 |
| 6,708,840 | B2 * | 3/2004 | Grinberg | 221/34 |
| D505,036 | S | 5/2005 | Wilfong, Jr. | |
| 6,955,276 | B2 * | 10/2005 | Grinberg | 221/34 |
| D547,580 | S | 7/2007 | Wilfong, Jr. | |
| D552,901 | S | 10/2007 | Wilfong, Jr. et al. | |
| 7,624,881 | B2 | 12/2009 | Wilfong, Jr. | |
| 8,210,354 | B2 * | 7/2012 | Alvarado et al. | 206/554 |
| 8,550,314 | B2 * | 10/2013 | Kelly et al. | 223/111 |
| 8,960,493 | B1 | 2/2015 | Dennison et al. | |
| 2006/0021956 | A1 | 2/2006 | Wilfong, Jr. | |
| 2006/0049199 | A1 * | 3/2006 | West | 221/26 |
| 2007/0094766 | A1 * | 5/2007 | Liu | 2/159 |
| 2007/0186515 | A1 | 8/2007 | Ruetten et al. | |
| 2008/0128465 | A1 | 6/2008 | Wilfong | |
| 2010/0021088 | A1 | 1/2010 | Wilfong, Jr. | |
| 2010/0316309 | A1 | 12/2010 | Wilfong | |
| 2012/0024884 | A1 | 2/2012 | Wilfong | |
| 2013/0134615 | A1 | 5/2013 | Wilfong, Jr. | |

OTHER PUBLICATIONS

USPTO; Notice of Allowance dated Dec. 22, 2014 in U.S. Appl. No. 14/331,061.

\* cited by examiner

METHOD AND APPARATUS FOR DISPOSABLE GLOVE DISPENSING

CLAIM OF PRIORITY

This application is a continuation of U.S. patent application Ser. No. 14/331,061, filed Jul. 14, 2014, entitled "METHOD AND APPARATUS FOR DISPOSABLE GLOVE DISPENSING," and claims priority to U.S. Provisional Patent Application Ser. No. 61/870,223, filed Aug. 26, 2013, entitled "METHOD AND APPARATUS FOR DISPOSABLE GLOVE DISPENSING," which are each hereby incorporated by reference.

BACKGROUND

Medical professionals, restaurant employees, and any other individual that handles food, chemicals, samples, or in any way is attempting to prevent the spread of germs cannot be sure they are operating effectively if the outside of a glove is touched prior to the user putting the gloves on their hands. Thus, it is desirable to have a delivery method and apparatus for allowing the user to insert their hands directly into an open glove without contaminating the glove outer surface.

SUMMARY

A disposable glove dispensing system may allow for a user to efficiently put on a disposable glove without touching the outside of the glove. In various embodiments, a disposable glove may comprise an opening for hand entry having a first opening edge and a second opening edge, a first interconnection point located near the first opening edge, wherein the first interconnection point attaches the disposable glove to a first adjacent disposable glove, and a second interconnection point located near the second opening edge. The second interconnection point may attach the disposable glove to a second adjacent disposable glove, wherein the disposable glove is positioned between the first adjacent disposable glove and the second adjacent disposable glove.

Furthermore, in various embodiments, a disposable glove dispensing system may comprise a pack of disposable gloves, where an individual disposable glove of the pack of disposable gloves is interconnected to adjacent disposable gloves, and a glove dispenser comprising a first glove hanger and a second glove hanger, where the pack of disposable gloves hang from the first glove hanger and the second glove hanger. Moreover, the glove dispenser may further comprise a main body connected to the first glove hanger and the second glove hanger, and further comprise a support member connected to the main body.

Moreover, in various embodiments, a method of dispensing a disposable glove is provided. A method of dispensing a disposable glove may include opening a disposable glove having a first opening edge and a second opening edge. The disposable glove may hang from a glove dispenser having a first glove hanger and a second glove hanger. The disposable glove also may be attached to an adjacent disposable glove by an interconnection point located near one of the first opening edge or the second opening edge. The method may further include inserting a hand into the disposable glove, tearing the interconnection point, and removing the disposable glove from the glove dispenser.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

The detailed description herein makes use of various exemplary embodiments to assist in disclosing the present invention. While these exemplary embodiments are described in sufficient detail to enable those skilled in the art to practice the invention, it should be understood that other embodiments may be realized and that modifications of structures, arrangements, applications, proportions, elements, materials, or components used in the practice of the instant invention, in addition to those not specifically recited, can be varied or otherwise particularly adapted to specific environments, manufacturing specifications, design parameters or other operating requirements without departing from the scope of the present invention and are intended to be included in this disclosure. Thus, the detailed description herein is presented for purposes of illustration only and not of limitation.

For the sake of brevity, conventional techniques for manufacturing and construction may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical method of construction.

Disclosed herein are one or more apparatuses and methods for inserting hands into disposable gloves without touching the outside of the gloves. This is beneficial for use in different industries, such as restaurant or other food-related industries. Virtually every fast food chain in the world requires all employees coming into contact with ingredients or food to use multiple pairs of plastic gloves each and every day. Touching the outside of the gloves can contaminate the surface and reduce the effectiveness of using the gloves. The disclosure can also have applications in the medical industry, which includes medical hospitals/clinics, long-term care facilities, outpatient surgical centers, doctor offices, dental offices, laboratories, and veterinary clinics. Furthermore, the disclosed methods and apparatuses could also be used in the home.

The disposable gloves as discussed herein can include gloves made of latex, nitrile, polyethylene, polyvinyl chloride, vinyl, and other suitable materials. The disposable gloves may also have different thicknesses of the materials for reducing contamination. For example, gloves for medical applications can be thicker than gloves for food handling applications. The disposable gloves can come in multiple packs of different sizes, such as small, medium, or large, and the like.

Figure 1:
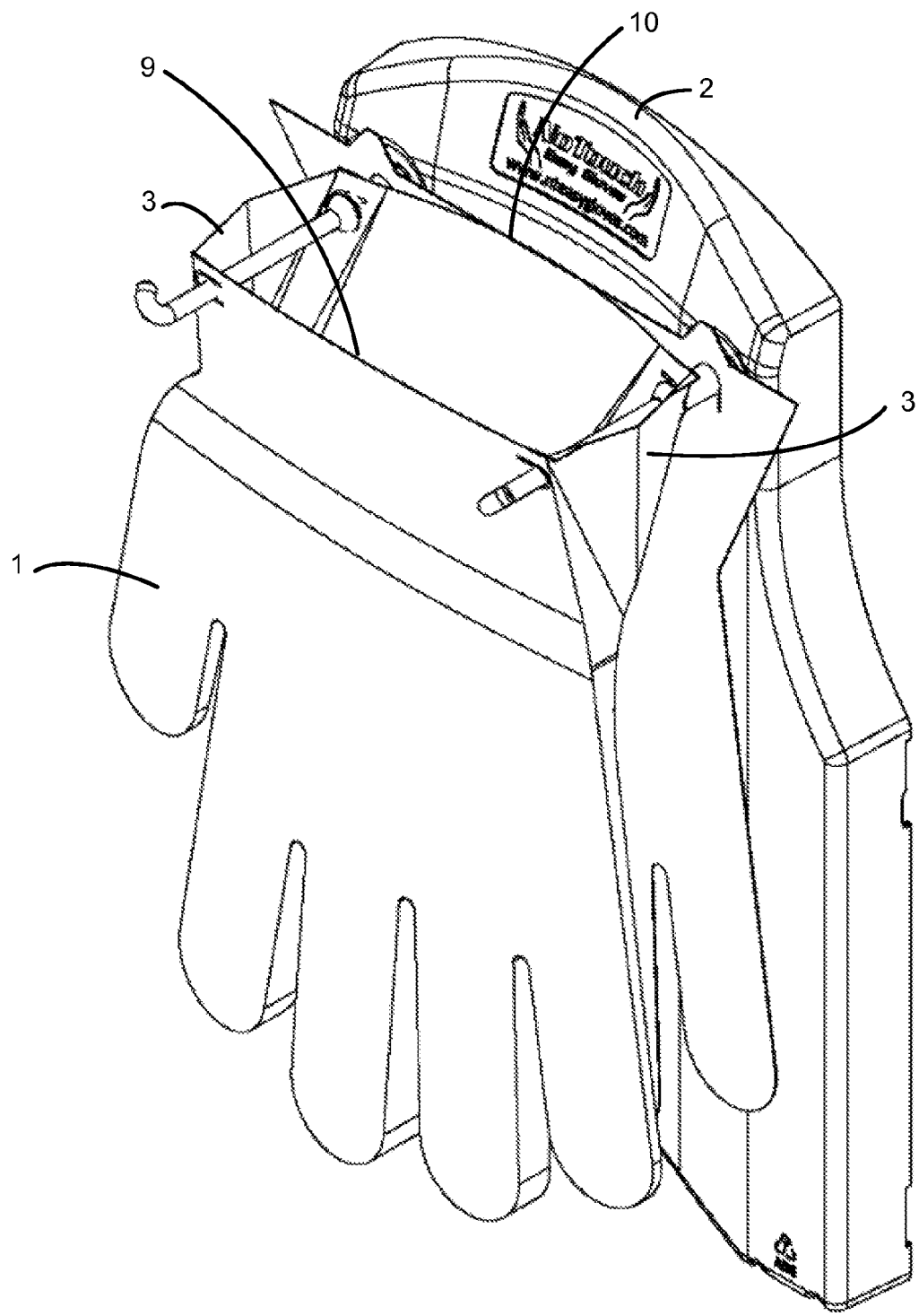
FIG. 1 illustrates a perspective view of a disposable glove pack and a glove dispenser, in accordance with various embodiments.
Figure 2:
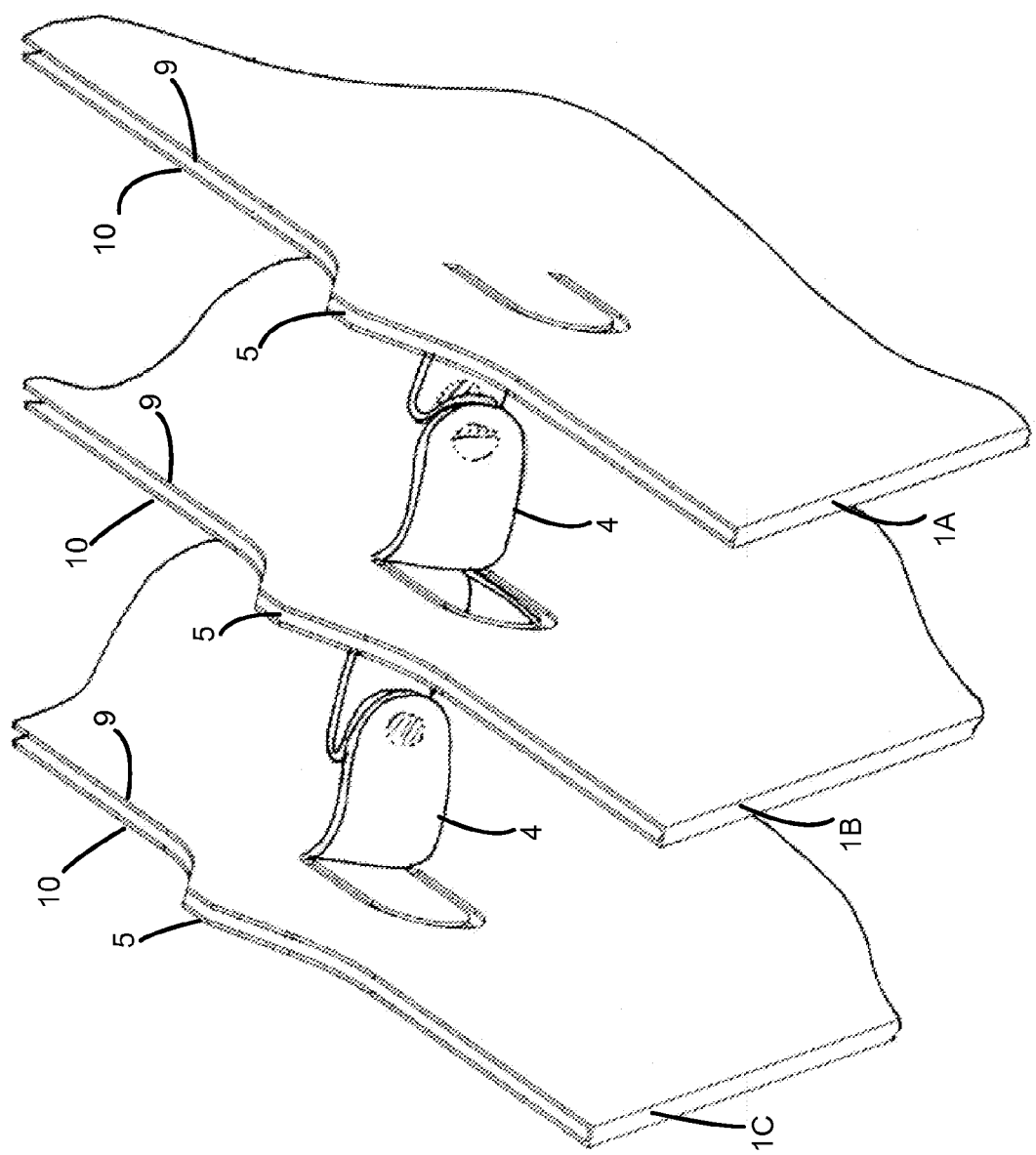
FIG. 2 illustrates a close-up perspective view of a disposable glove pack and interconnection point(s), in accordance with various embodiments.

In accordance with various embodiments and with reference to FIG. 1, a disposable glove dispensing system may comprise a pack of disposable gloves 1 attached to a glove dispenser 2. The disposable glove pack can comprise several gloves. Each glove can be flat and connected between other adjacent disposable gloves 1 at one or more connection points. With reference to FIGS. 1 and 2, each glove may have a first opening edge 9 on a forward side of the disposable glove (see also, FIGS. 2, 5A, 11A, 13A, 14A, 15B) and a second opening edge 10 on an aft side of the disposable glove (see also, FIGS. 2, 5A, 11A, 13A, 14A, 15B). When the glove is opened, the first opening edge 9 and the second opening edge 10 are spread from one another so that a hand may be inserted between the first opening edge 9 and the second opening edge 10 and into the body of the glove 1.

Figure 5A:
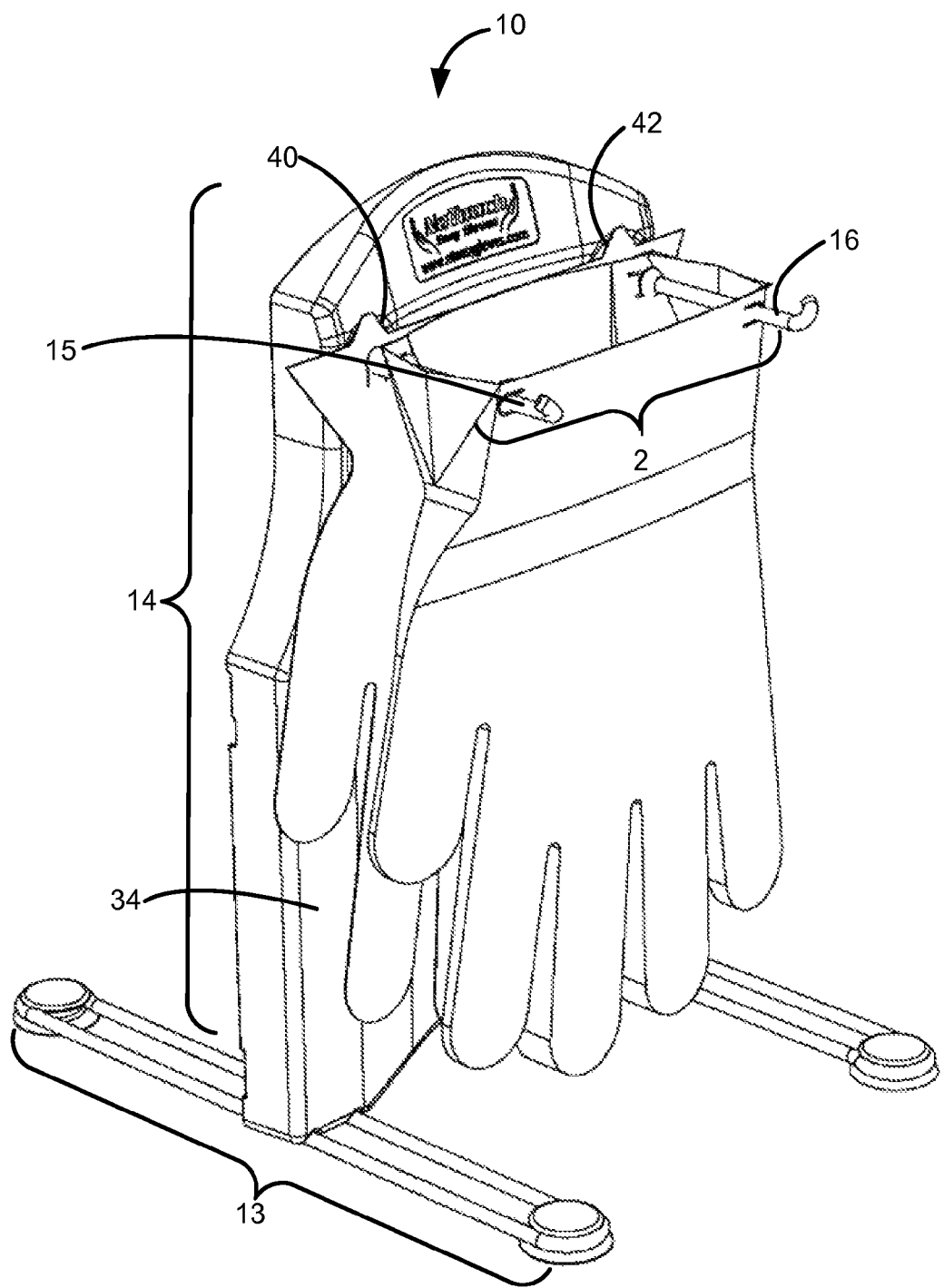
FIG. 5A illustrates a perspective view of a disposable glove pack and a glove dispenser, in accordance with various embodiments.
Figure 5B:
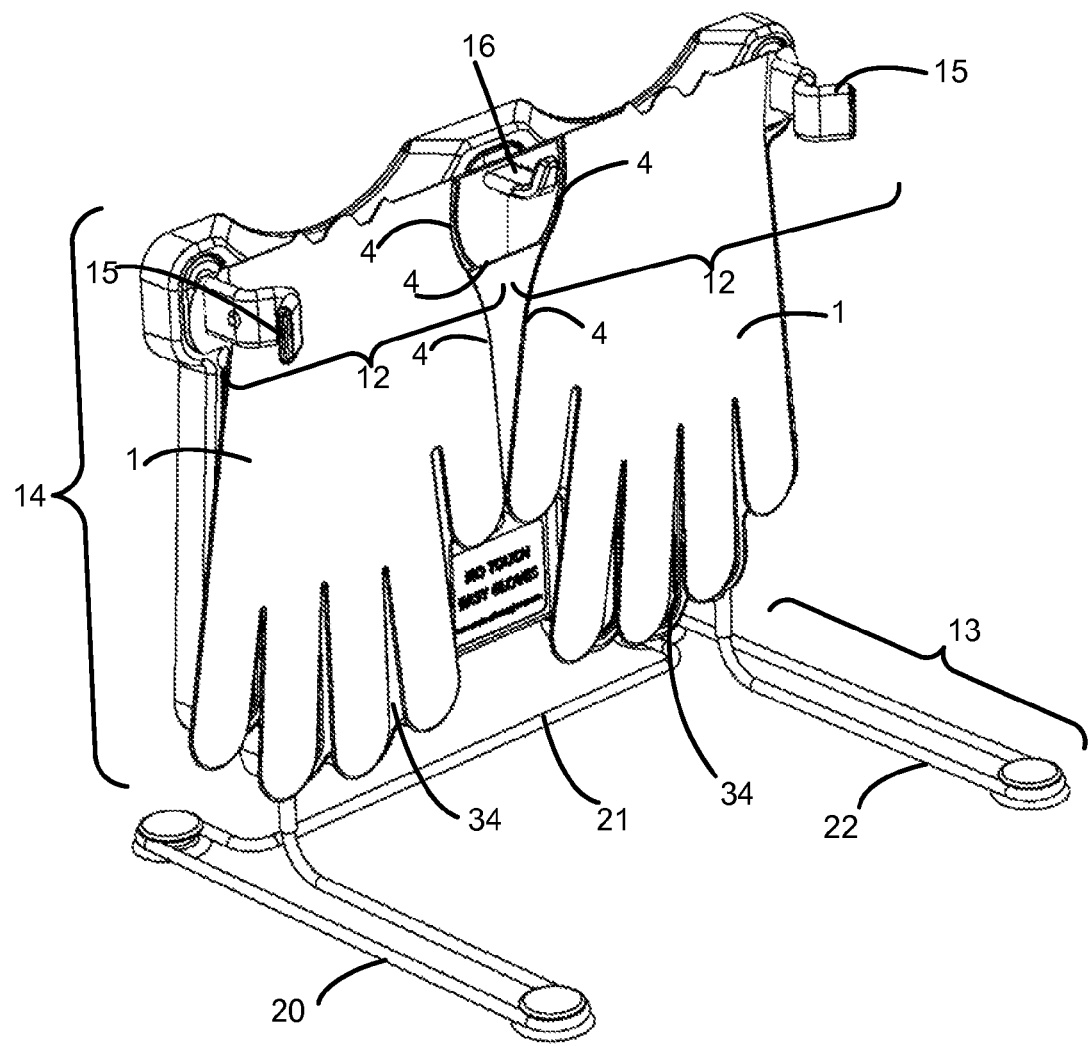
FIG. 5B illustrates a perspective view of a disposable glove pack and a side-by-side glove dispenser, in accordance with various embodiments.

In accordance with various embodiments, FIG. 5B illustrates two adjacent disposable gloves 1 connected by an inner support sheet 6. The inner support sheet 6 may provide strength and stability to the gloves when hanging from glove dispenser 2, yet also facilitate the easy removal of the gloves. For example, interconnection point(s) 4 may be spaced around the perimeter of inner support sheet 6, providing regions wherein the force of a user's hand when pulling the gloves away from the glove dispenser 2 may be concentrated, facilitating local tearing at interconnection point(s) 4 and easy removal of the gloves from the glove dispenser 2.

In accordance with various embodiments, FIG. 2 illustrates a close-up view of exemplary interconnection point(s) between multiple gloves. As shown in FIG. 2, in various embodiments, a first disposable glove 1A may have an interconnection point 4 to an adjacent second disposable glove 1B, and the second disposable glove 1B may have an interconnection point 4 to an adjacent third disposable glove 1C. As the first disposable glove 1A is drawn away from the glove pack, the interconnection point(s) 4 pull the adjacent second glove 1B open, staging the adjacent second glove 1B ready to receive the next hand. In this manner, a disposable glove remains ready and available for a person to put on the disposable gloves without having to touch the outside of the gloves.

Figure 3A:
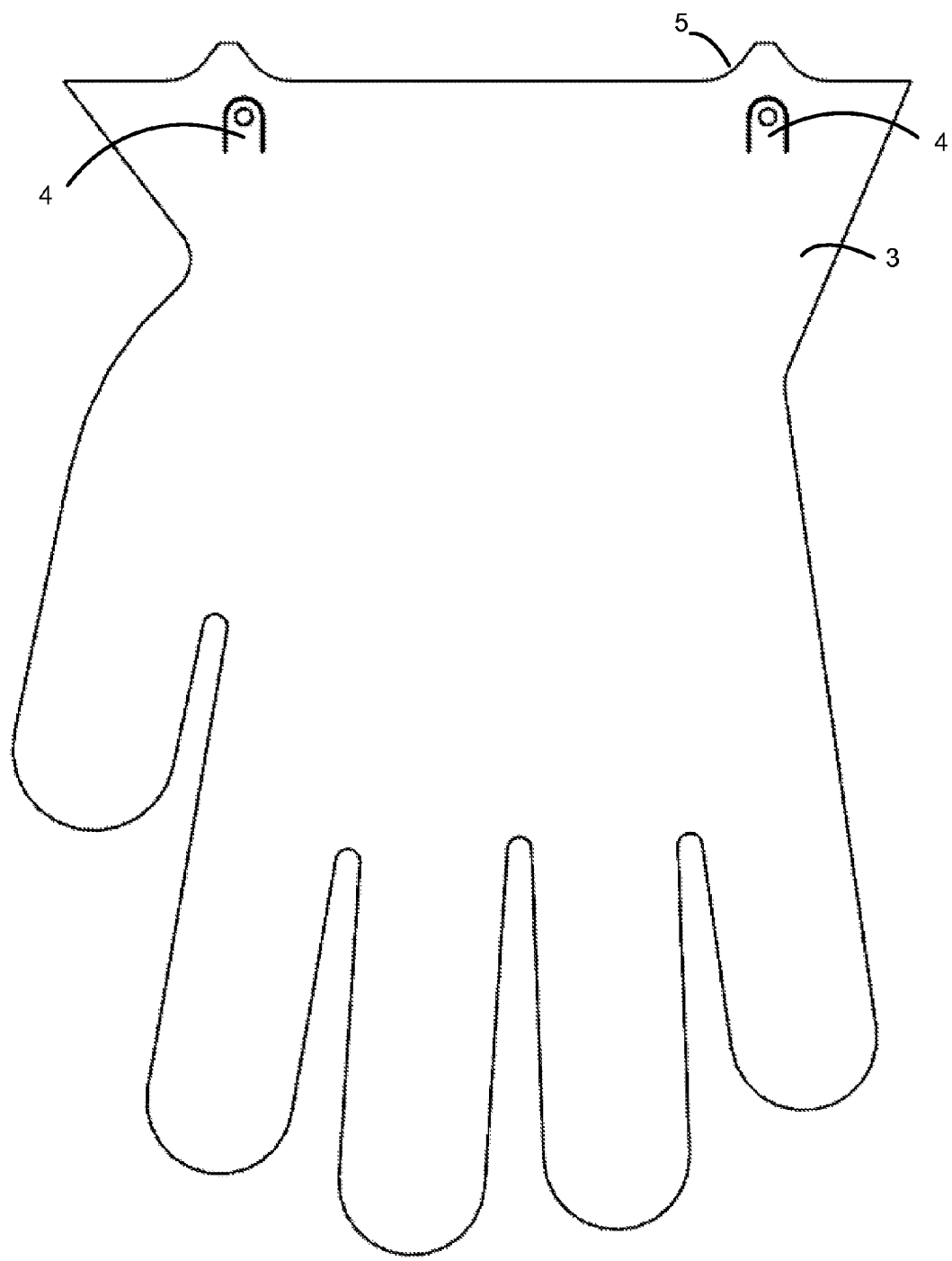
FIGS. 3A-B illustrate front views of exemplary disposable gloves, in accordance with various embodiments.
Figure 3B:
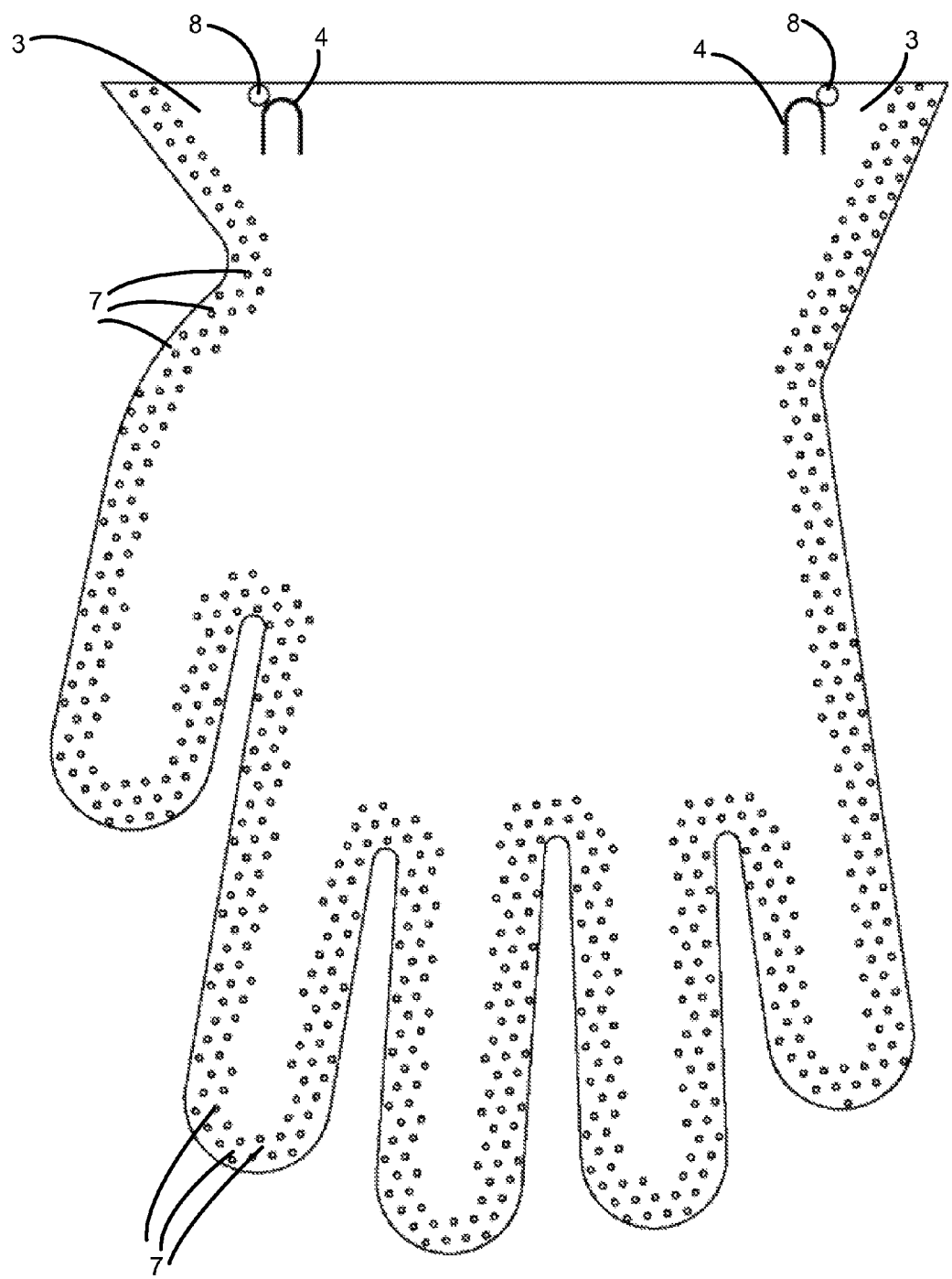

The interconnection point 4 may be located near a hanging point on a glove hanger, for example, as illustrated in FIGS. 2, 3A-B, and 5B. In various embodiments, the gloves may be separated, and thereby the interconnection point(s) 4 separated, by pulling the top edge of the glove along the axis of each glove hanger. As shown in FIGS. 2 and 3A-B, in various embodiments, the interconnection point 4 may be connected tabs from a punch-out of a hole for the glove hanger. In various embodiments, a glove hanger may be inserted into the punch-out hole, and the resulting tabs from the punch-out are retained and formed into the interconnection point(s). Alternatively, in various embodiments, an interconnection point 4 may occur anywhere along the top edge of the gloves. Furthermore, in various embodiments, the interconnection point(s) 4 can be perforated and have thinner plastic areas, with small connection points that may be easily broken. Additionally, the interconnection point(s) 4 may be connected via heat sealing, an adhesive, an interlock tab, or a combination thereof. When the interconnection point(s) 4 are pulled, the interconnection point(s) 4 may separate by introducing sheer force to separate the adhesive or weld dots on each interconnection point 4.

Figure 15A:
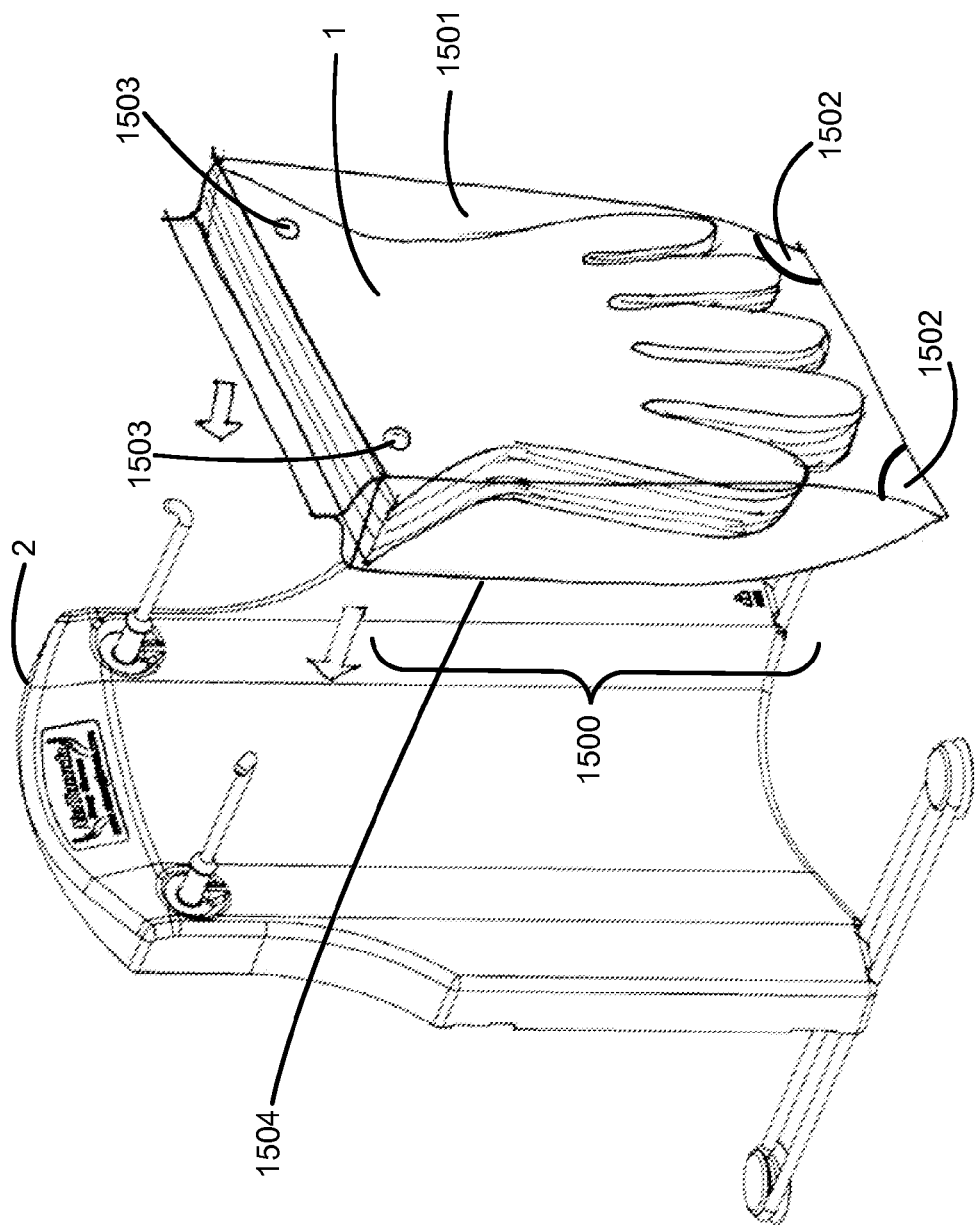
FIGS. 15A-B illustrate perspective views of a disposable glove pack having a cover and a glove dispenser, in accordance with various embodiments.
Figure 15B:
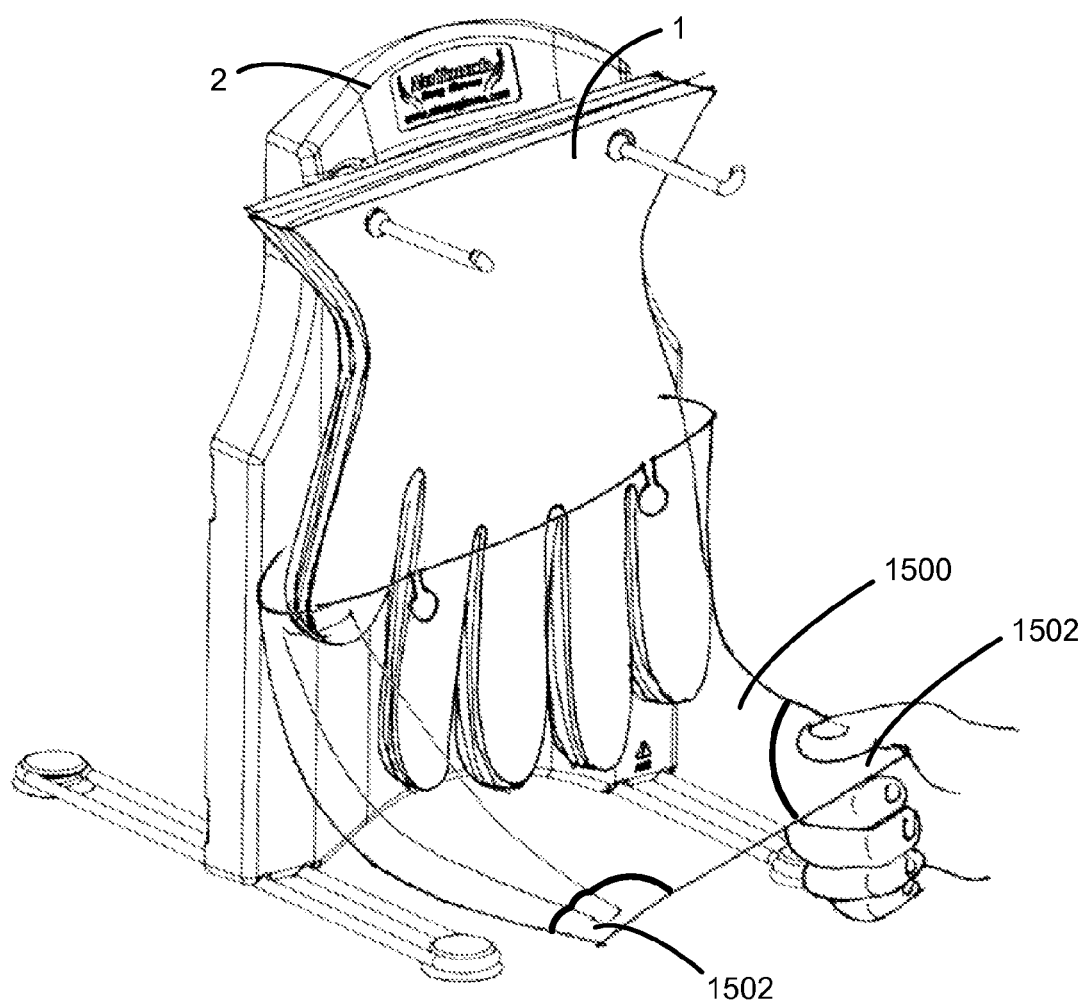

With momentary reference to FIG. 3B, in various embodiments, the gloves may individually further comprise one or more tear points 8 near the top edge. A tear point 8 may comprise an aperture through the glove 1, or thinner regions, or perforations or other like structures for removably coupling gloves to a sanitary sealed film glove package 1500 (see FIG. 15A-B). This aperture may permit a sanitary sealed film glove package 1500 (see FIGS. 15A-B) to interface with the gloves. For example, a portion of the glove package that is disposed in contact with the outermost glove may be attached to a portion of the glove package that is disposed in contact with the innermost glove. For example, the glove package may comprise a metallic material aligned with the tear point 8. The metallic material may be warmed by RF welding so that the portion of the glove package disposed in contact with the outermost glove melts to the portion of the glove package disposed in contact with the inner most glove, through the tear point 8. Other embodiments may comprise tear point(s) 8 located anywhere proximate the top edge, e.g., a glove 1 may individually comprise two tear points 8 disposed along the top edge, although a glove 1 may comprise any number of tear points 8 disposed at any position to facilitate removably coupling gloves to a sanitary sealed film glove package 1500 (see FIGS. 15A-B).

With continued reference to FIGS. 2 and 3A, the disposable gloves 1A, 1B, 1C may individually further comprise a pull tab 5 on the top edge. The pull tab 5 may be used to facilitate further opening of a disposable glove by pulling of the pull tab 5. A user may be able to pull the pull tab 5 to open the glove with minimal contact between the glove and the user. With reference to FIG. 3C, further embodiments may omit the pull tab 5.

In accordance with various embodiments and with renewed reference to FIGS. 1 and 3A-B, the disposable glove 1 may further comprise one or more gussets 3 located on one or more sides of the first opening edge 9 and the second opening edge 10 making up the glove opening. The extra material of the gusset 3 may allow easier separation of the opening by facilitating expansion of the glove opening when the glove is hanging. Specifically, the gussets 3 can provide additional slack to the glove opening such that the glove may opened with little or no resistance and allowing an opening that is sufficiently wide for hand insertion. The gussets 3 may provide additional linear edge to the opening of the glove thereby allowing the distance from the first opening edge 9 and the second opening edge 10 to increase as the glove is opened. In various embodiments, the gussets 3 are triangular in shape though other shapes, such as rhomboid or parabolic, may be used. Additionally, the gusset 3 may be in-board or out-board of the hanging points of the glove hanger. An out-board gusset results in the extra gusset material being outside of the glove opening, creating a flared glove opening. Similarly, the in-board gusset results in the extra gusset material being folded inside the glove opening.

Though the gloves may come in different sizes (small, medium, large, etc.) as previously mentioned and with reference to FIG. 3B, a disposable glove 1 may also be designed to better fit a user's hand. In various embodiments, the disposable glove 1 may comprise tack points 7 around the inside perimeter. For example, the glove may have tack points near the wrist area and/or around the perimeter of the fingers. The tack points 7 may be formed using light tack adhesion to create a series of interconnected points. As the user inserts a hand, the tack points 7 break to accommodate the size of the user's hand. Any unbroken tack points 7 provide a more snug fit around the hand.

In accordance with various embodiments, and with reference to FIGS. 4 and 5A-C, a glove dispenser 2 may comprise a main body 14, a support member 13, and a glove retention member 12. In various embodiments, the glove dispenser 2 is a unitary body, or an assembly of different pieces, or may comprise any arrangement of elements whereby gloves may be dispensed.

The glove dispenser 2 may comprise a main body 14 standing upright and an attached support member 13 to stabilize the main body 14. Alternatively, the glove dispenser 2 may comprise a self-supporting unitary body joined with a glove retention member 12. As discussed further herein, the glove retention member 12 may be connected to the main body 14 and may support gloves to be dispensed. In this manner, the main body 14 may be sufficiently tall that it may hold the gloves vertically. In various embodiments, the main body 14 may comprise a molded plastic body, may comprise metal or ceramic, may be a bent metal channel, may comprise a machined part, or may be any structure adapted to support the glove retention member 12.

Figure 5C:
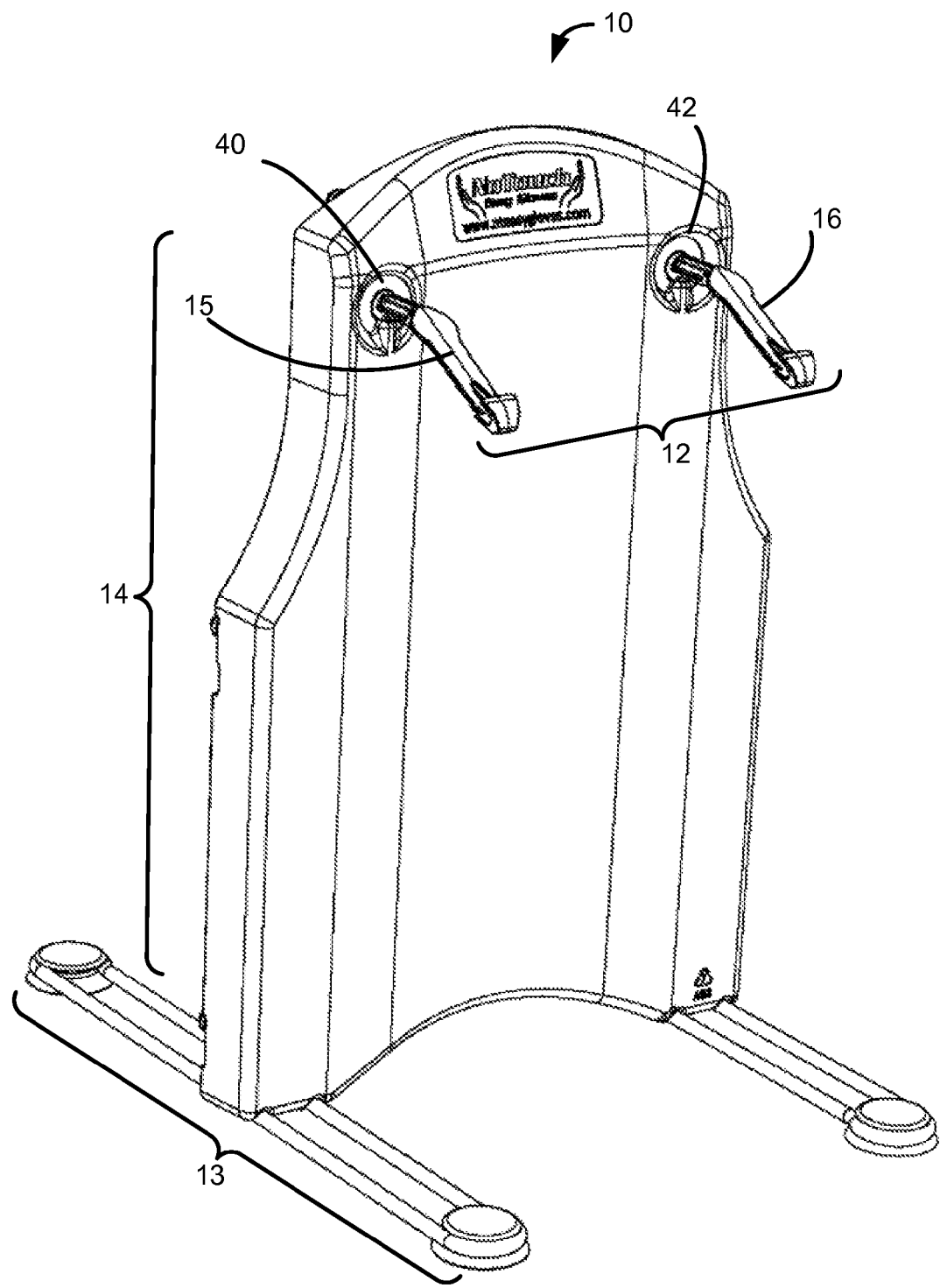
FIG. 5C illustrates a perspective view of a glove dispenser with glove hangers having a widened retention portion, in accordance with various embodiments.

Furthermore, in various embodiments and with reference to FIGS. 5A and 5C, the glove retention member 12 may comprise a pair of glove hangers, for example, a first glove hanger 15 and a second glove hanger 16. For example, a pair of glove hangers may extend normal to a face of the main body 14. In this manner, gloves may be connected to the glove hangers and supported thereby. In one embodiment, the first glove hanger 15 is parallel to the second glove hanger 16. In another embodiment, the first glove hanger 15 and the second glove hanger 16 may be angled towards each other, with the hangers narrowing towards each other away from the main body 14. In this manner, the gloves may be taut near the main body 14 and have more slack near the hanger ends to be easier to insert a hand. In various embodiments, the glove retention member 12 may comprise one glove hanger, three glove hangers, or any number of glove hangers configured to support gloves. Moreover, the glove retention member 12 may comprise tabs, or clips, or hooks, or any other apparatus or combination of apparatuses designed to support at least one glove. In various embodiments, the glove dispenser 2 may comprise a single glove retention member 12 comprising a pair of glove hangers. However, in various other embodiments, the glove dispenser 2 may comprise two to four glove retention members 12, or any other suitable number of glove retention members 12, so that multiple gloves may be separately supported by the glove dispenser 2.

In various embodiments and with reference to FIG. 5B, the glove dispenser 2 may comprise two glove retention members 12, which may comprise various combinations of glove hangers. For example, the two glove retention members 12 may share a second glove hanger 16. Thus, one glove retention member 12 may comprise a left side first glove hanger 15, a centrally positioned second glove hanger 16. The other glove retention member 12 may comprise a right side first glove hanger 15 and the centrally disposed second glove hanger 16 which is shared by the two glove retention members 12. In other embodiments, the glove retention member 12 comprises two complete pairs of glove hangers, so that a first glove hanger 15 and a second glove hanger 16 support each disposable glove 1. The glove hangers may extend normal to a face of the main body 14. In this manner, disposable gloves 1 may be connected to the glove hangers and supported thereby. In one embodiment, the glove hangers are parallel. In another embodiment, the first glove hanger 15 may be angled outwardly from the main body 14 and the second glove hanger 16 may be angled upwardly from the main body 14. In this manner, the gloves may be prevented from sliding off of the glove retention hangers. In various embodiments, the glove retention member 12 may comprise one glove hanger, three glove hangers, or any number of glove hangers configured to support gloves. Moreover, the glove retention member 12 may comprise tabs, or clips, or hooks, or any other apparatus or combination of apparatuses designed to support at least one glove. In various embodiments, the glove dispenser 2 may comprise a single glove retention member 12 comprising a pair of glove hangers. However, in various other embodiments, the glove dispenser 2 may comprise two to four glove retention members 12, or any other suitable number of glove retention members 12, so that multiple gloves may be separately supported by the glove dispenser 2. In still other embodiments, as illustrated in FIG. 5B, the glove dispenser 2 may comprise two glove retention members 12 sharing a centrally positioned second glove hanger 16, so that multiple gloves may be supported by the glove dispenser 2.

In various embodiments, and with reference to FIGS. 5A and 5C, the support member 13 may comprise four supporting legs disposed perpendicular to a Y-Z plane intersecting the main body 14, or in any direction whereby the glove dispenser 2 may be supported. For example, if the main body 14 may be said to be standing upright (e.g., vertically), the support member 13 may be said to be lying beneath the main body 14 (e.g., horizontally). If the Y-Z plane may be said to intersect the main body 14, the legs may be said to lie in the X-Z plane, and the X-Y plane may be said to bisect the main body 14 as referenced in FIG. 5. In various embodiments, the support member 13 prevents the main body 14 from toppling. In various embodiments, the support member 13 may comprise any number of legs, or may not comprise legs but may comprise a singular leg, for example, a large planar leg, or may comprise three legs, for example a tripod. In various embodiments, and with reference to FIG. 5B, the support member 13 may comprise two supporting legs disposed perpendicular to a Y-Z plane intersecting the main body 14, or in any direction whereby the glove dispenser 2 may be supported. The support member 13 may be removable, for instance, to permit compact shipping and storage.

The main body 14 may comprise a unitary plastic body, for example, a main body 14 may support the glove retention member 12. A main body 14 may comprise a rectangular body, or a triangular body, or a wire frame body, or may comprise any arrangement of elements whereby the glove retention member 12 may be disposed at a position whereby gloves may be supported without unwanted interference from surrounding objects or environments.

Having described various aspects of the main body 14 of the glove dispenser 2, the glove dispenser 2 also may comprise a glove retention member 12. With reference to FIGS. 5A, 5C, 6A, and 6B, the glove retention member 12 may comprise a first glove hanger 15 and a second glove hanger 16. In various embodiments, the first glove hanger 15 and/or the second glove hanger 16 are each disposed extending normal (e.g., perpendicularly) from a face of the main body 14. While various embodiments are depicted herein having a first glove hanger 15 and a second glove hanger 16, it may be appreciated that one glove hanger, or three glove hangers, or four glove hangers, or any number of glove hangers may be implemented. In various embodiments, the first glove hanger 15 and the second glove hanger 16 are spaced equidistant from a line passing through the center of the main body 14 of the base (i.e., the X-Y plane). Moreover, the first glove hanger 15 and the second glove hanger 16 may be mirrors of one another, for example, as discussed further wherein, each glove hanger may have a hanger angle 45 (FIG. 7A) whereby the glove hangers are both angled outward from a line passing through the center of the main body 14, or whereby the glove hangers are angled at a hanger angle 45 (FIG. 7D) approximating a right angle from a line passing through the center of the main body 14. In further embodiments, with reference to FIG. 5B, multiple glove retention members 12 may be positioned so that they share one or more glove hangers. For example, with momentary emphasis on FIG. 5B, two glove retention members 12 may share a centrally positioned second glove hanger 16.

Figure 4:
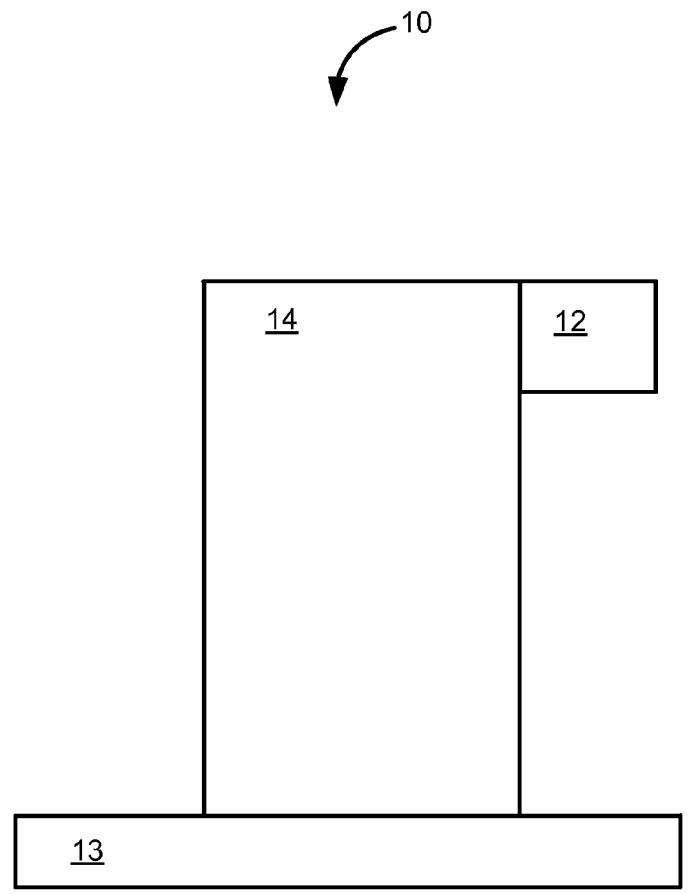
FIG. 4 illustrates a block figure of an exemplary view of a glove dispenser, in accordance with various embodiments.

With reference now to FIGS. 4, 5A and C, and 6A-B, the support member 13 may comprise legs. For example, the support member 13 may comprise a first forward leg 20, a second forward leg 22, a first aft leg 24, and a second aft leg 26. The first forward leg 20 and the second forward leg 22 may be spaced along one face of the main body 14, and the first aft leg 24 and the second aft leg 26 may be spaced along a second face of the main body 14. These faces may be parallel, for example, parallel opposite sides of the main body 14. With momentary reference to FIG. 9, in various embodiments, legs may be made in pairs, for example, the first forward leg 20 and the second forward leg 22 may be a pair, and the first aft leg 24 and the second aft leg 26 may be a pair. Each pair may comprise a single bent piece of metal, for example, a stiff metal wire. In various embodiments, each leg has a foot 50. Alternatively, with reference to FIG. 5B, the support member 13 may comprise a first forward leg 20 and a second forward leg 22. The support member 13 may further comprise an aft support bar 21 extending perpendicular to the first forward leg 20 and the second forward leg 22 and behind the main body 14, eliminating the need for aft legs. The various legs may be removable, for instance, to permit compact shipping and storage.

In various embodiments, the foot 50 may comprise a circular disc. In one example, the foot 50 may be a suction cup to attach the legs to a flat surface. In another example, the foot 50 may be the same suction cup but may be reversible to provide a friction connection between the legs and the flat surface. Alternatively, the foot 50 may comprise an integral portion of a leg, for example the first forward leg 20, the second forward leg 22, the first aft leg 24 or the second aft leg 26. Furthermore, in various embodiments, the foot 50 may be circular, or square, or oval, or trapezoidal, or may comprise any shape or combination of shapes configured to provide stability. The foot 50 may extend below the leg, for example, to diminish wobble caused by dimensional overconstraint of the support member 13 when resting on a surface, for example, a countertop. In various embodiments, the foot 50 is rubber, though it may be plastic or any other material suitable to provide support to the glove dispenser 2 and friction resistance to the surface on which it rests.

Figure 6A:
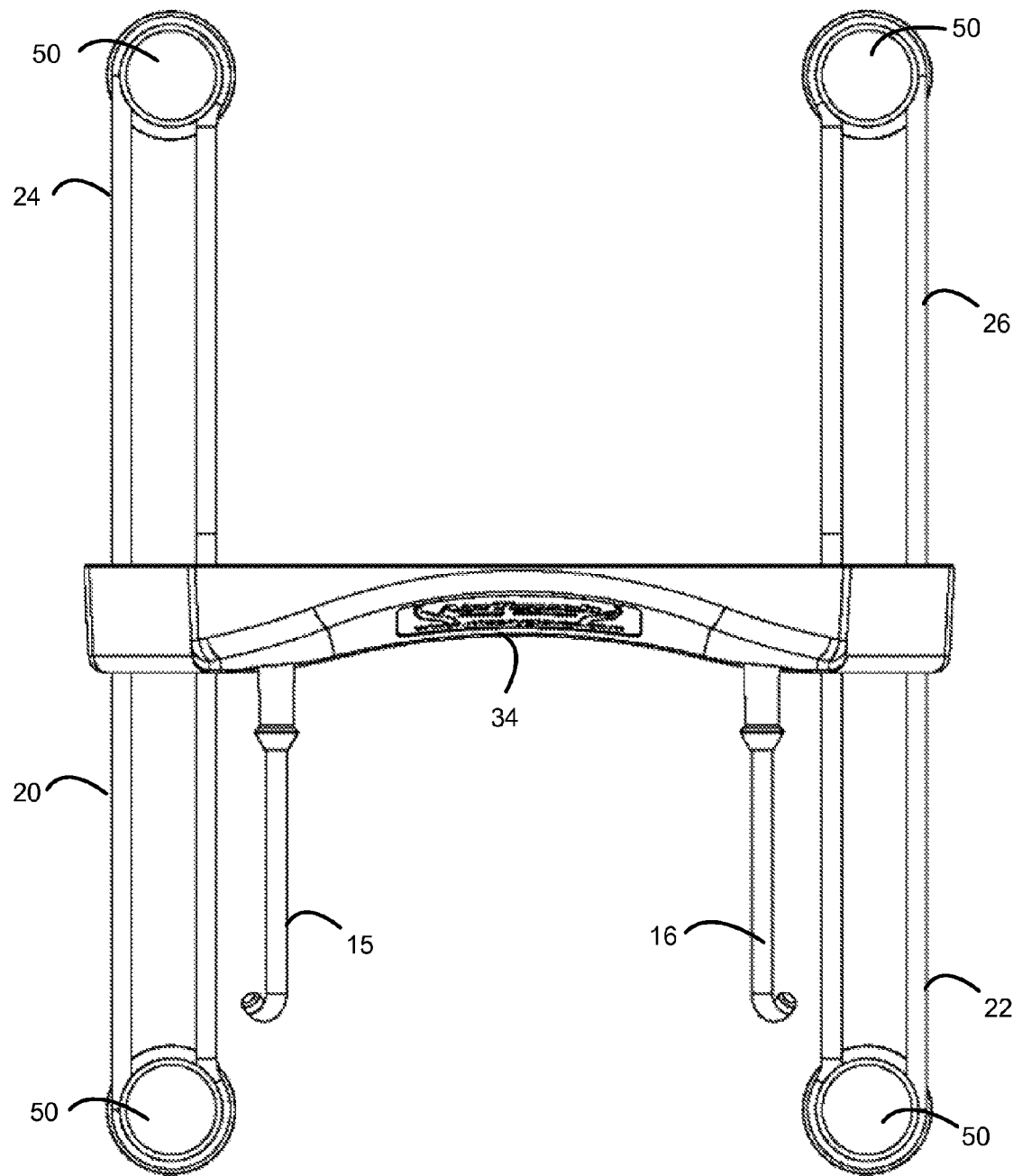
FIGS. 6A-B illustrate top-down views of dispensing stands, in accordance with various embodiments.
Figure 6B:
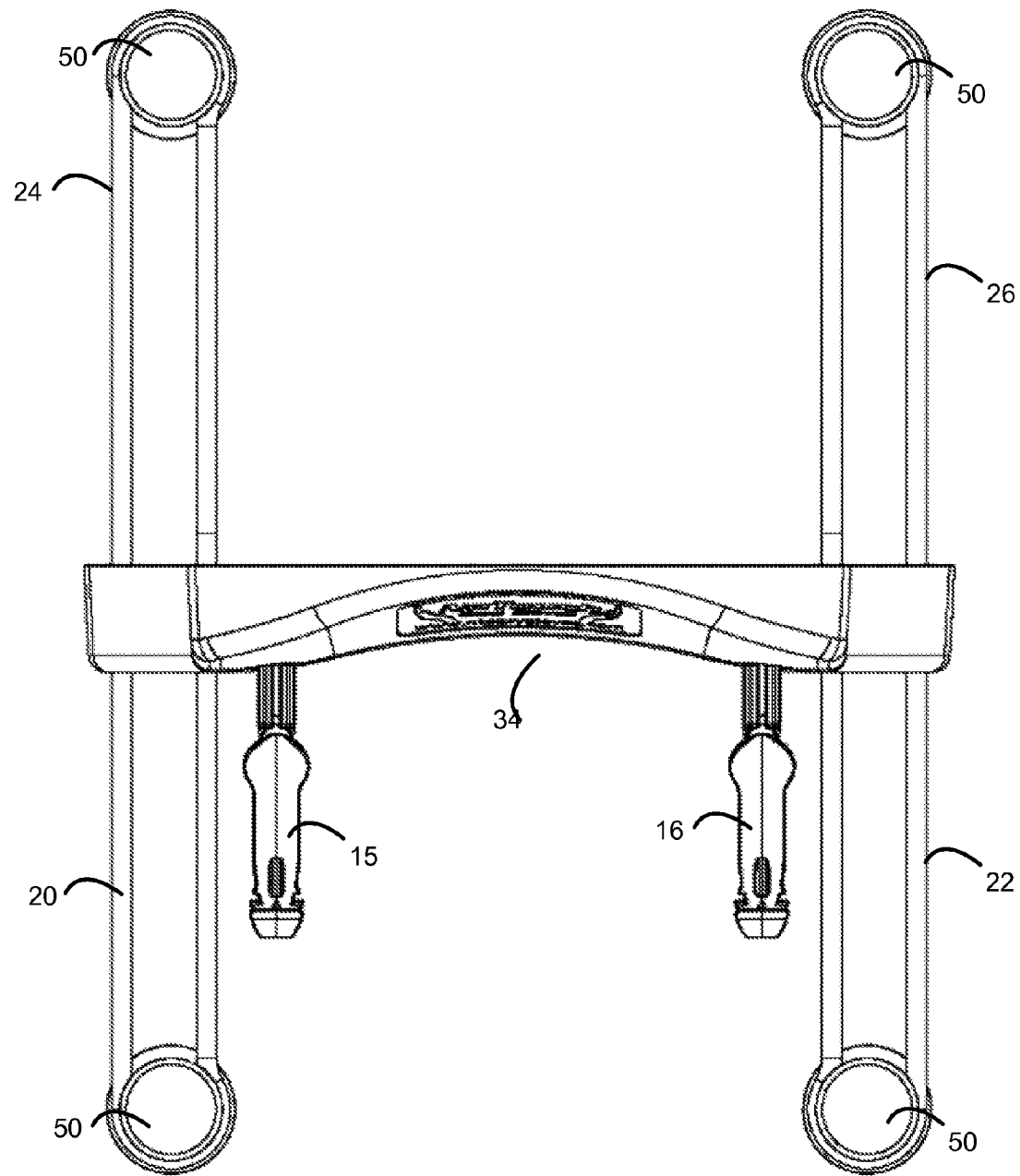
Figure 9:
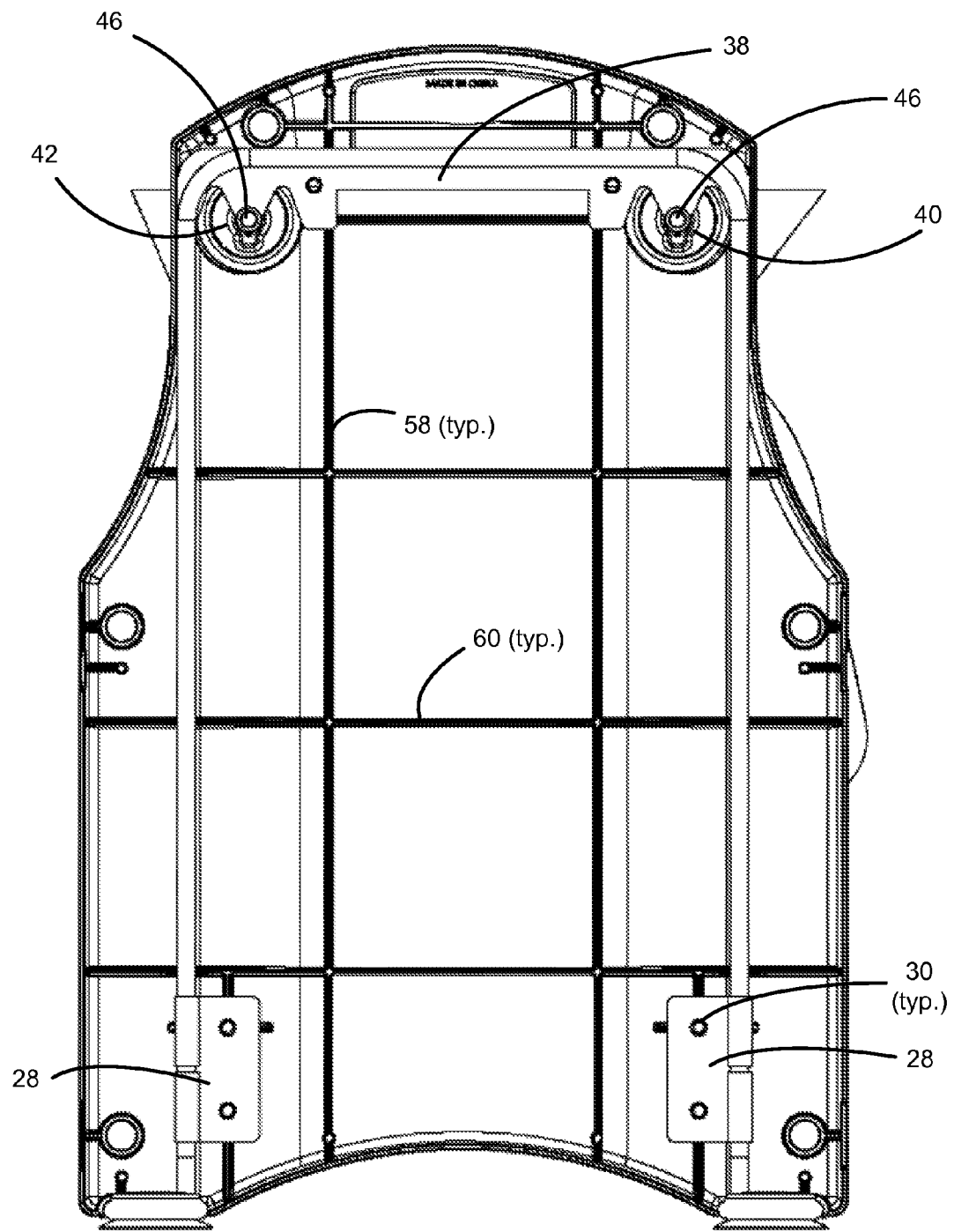
FIG. 9 illustrates a back view of a glove dispenser, in accordance with various embodiments.

With continuing reference to FIGS. 4 and 6A-B and with additional reference to FIG. 9, the support member 13 may also comprise a support member base attachment element 28. The support member base attachment element 28 may comprise a tab attached to a portion of the support member 13. Further, the support member base attachment element 28 being a tab may comprise one or more holes 30 to facilitate connecting the tab to the main body 14. In various embodiments, the one or more holes 30 correspond to an aperture disposed within the support member base attachment element 28. In this manner, a fastener may be inserted to hold the two elements in mechanical communication. Alternatively, the support member base attachment element 28 may comprise a plug, a stake, a glue pad, or any other mechanism intended to interface with the main body 14.

In some embodiments, the support member base attachment element 28 may be a tab connected to the wire comprising a leg. In some embodiments, the legs are made in pairs, for example, the first forward leg 20 and the second forward leg 22 may be a pair comprising a single piece of bent wire, and the support member base attachment element 28 may be a tab connected to the wire proximate to one of the legs. In various embodiments, the support member base attachment element 28 comprises a pair of metal tabs each attached to a different portion of the support member 13. For example, the support member base attachment element 28 may comprise a first tab attached to a first portion of the support member 13 and a second tab attached to a second portion of the support member 13. Thus, a tab may be positioned near each of the legs, for example, the first portion may be proximate to the first forward leg 20 and the second portion may be proximate to the second forward leg 22. Alternatively, the first portion may be proximate to the first aft leg 24 and the second portion may be proximate to the second aft leg 26. Moreover, one or more support member base attachment element 28 may be associated with each leg or pair of legs.

With reference to FIGS. 5A-C, 6A-B, and 9, in various embodiments, the main body 14 comprises a hanger interface plate 38 on the backside of the main body 14. The hanger interface plate 38 may comprise a metal plate disposed in contact with the first glove hanger 15 and the second glove hanger 16. The plate may limit the movement of the first glove hanger 15 and the second glove hanger 16. For example, each glove hanger may be articulable through a plane parallel to a face of the main body 14, for example, as discussed herein, a glove backstop face 34 of the main body 14. However, the hanger interface plate 38 may restrict the movement of the glove hangers, for example, preventing downward movement of the glove hanger (e.g., movement in the negative Y direction). As a result, the hanger may be ridged in the downward direction, but when struck by hands or with a body part, the hangers may flex to reduce the risk of injury. Moreover, the flexing may reduce the risk that such inadvertent contact would break the glove dispenser 2. The hanger interface plate 38 may be disposed in contact with both the first glove hanger 15 and the second glove hanger 16, or with just one glove hanger, or with any number of glove hangers.

With reference to FIGS. 5A-C and 6A-B, in various embodiments, the glove backstop face 34 may provide a surface against which gloves may rest as they hang from the glove retention member 12. The glove backstop face 34 may comprise a concave surface, for example at a top portion of the main body 14. For example, the glove backstop face 34 may comprise a chamfered and/or curved face resembling a curve of the back of a human hand. In this manner, the glove backstop face 34 may enhance the ease with which a hand may be inserted into a glove attached to the glove retention member 12. In various embodiments, glove backstop face 34 is planar. However, the glove backstop face 34 may comprise any shape whereby the user's hand may be more readily guided to access the glove attached to the glove retention member 12.

Additionally, in various embodiments and with reference to FIGS. 5A-C and 9, the main body 14 may comprise vertical strengthening ribs 58 and horizontal strengthening ribs 60 for providing support and strength. The main body 14 may comprise two vertical strengthening ribs 58, though any number of vertical strengthening ribs 58 may be implemented. Further, the main body 14 may comprise three horizontal strengthening ribs 60, though any number of horizontal strengthening ribs 60 may be implemented. The vertical strengthening rib 58 may comprise a unitary piece of material integral with the main body 14 and traversing a substantial length of the main body 14 parallel to the Y-axis. Similarly, the horizontal strengthening rib 60 may comprise a unitary piece of material integral with the main body 14 and traversing a length of the main body 14 parallel to the X-axis. At least one of the vertical strengthening ribs 58 and the horizontal strengthening ribs 60 may extend in the negative Z-direction, so that it forms a stringer running along a face of the main body 14. In this manner, the ribs may ameliorate bending and may provide reinforcement to the glove dispenser 2. The strengthening ribs 58, 60 may comprise any element adapted to ameliorate bending so as to strengthen the main body 14 and enhance rigidity in the Y-Z plane.

With reference to FIGS. 5A-C, 7A-B, 7D-E, and 9, the glove retention member 12 may further comprise a first glove hanger aperture 40 connected to the first glove hanger 15 and a second glove hanger aperture 42 connected to the second glove hanger 16. The first glove hanger aperture 40 and second glove hanger aperture 42 may individually comprise an aperture disposed in the glove backstop face 34 of the main body 14. For example, an aperture may be disposed linearly outward and upward of a geometric center point of the glove backstop face 34. In other words, the first and second glove hanger apertures 40, 42 may be disposed in the upper left corner and upper right corner, respectively, of the glove backstop face 34.

Figure 7A:
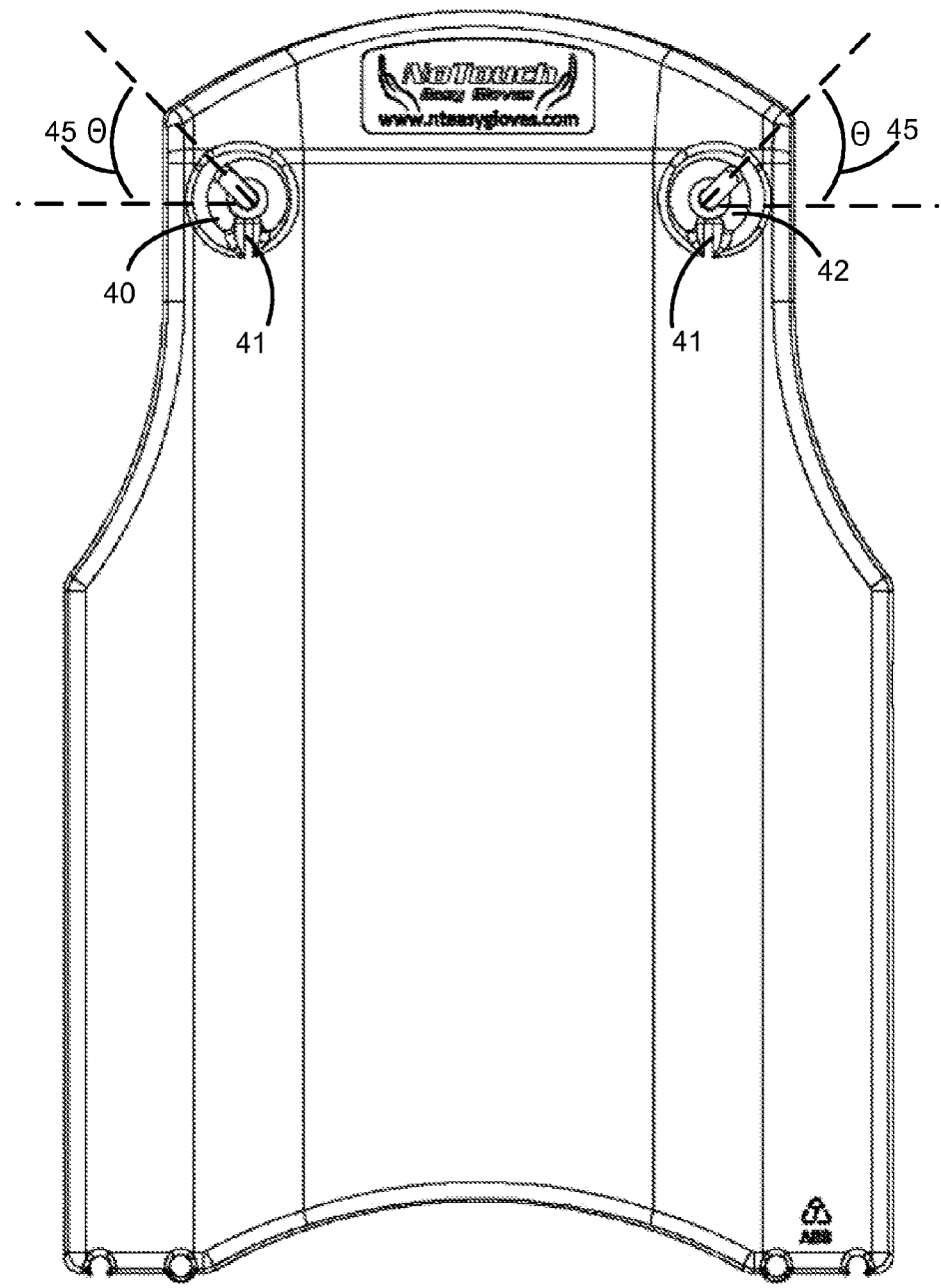
FIG. 7A illustrates a front view of a glove dispenser, in accordance with various embodiments.
Figure 7B:
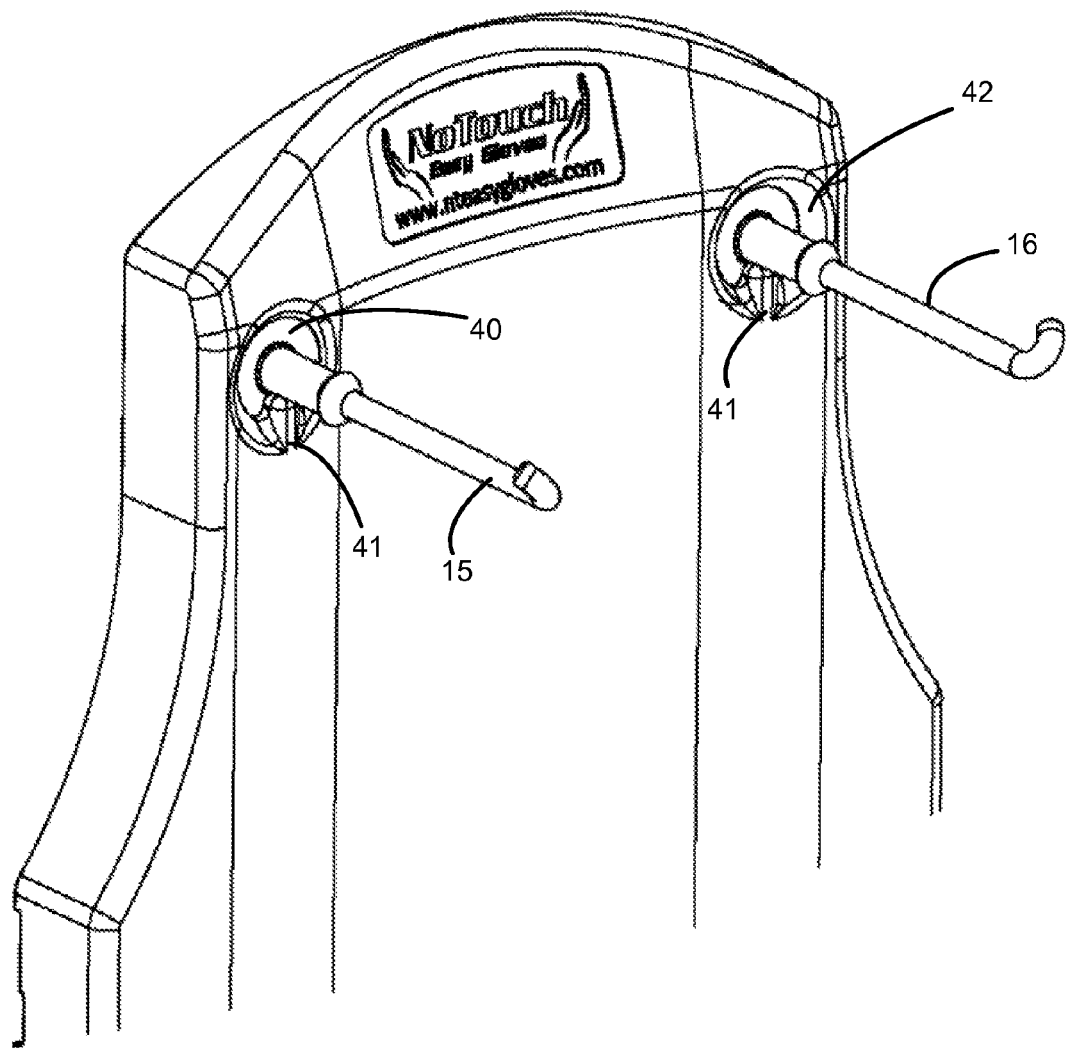
FIG. 7B illustrates a close-up perspective view of a glove dispenser and glove hangers, in accordance with various embodiments.
Figure 7C:
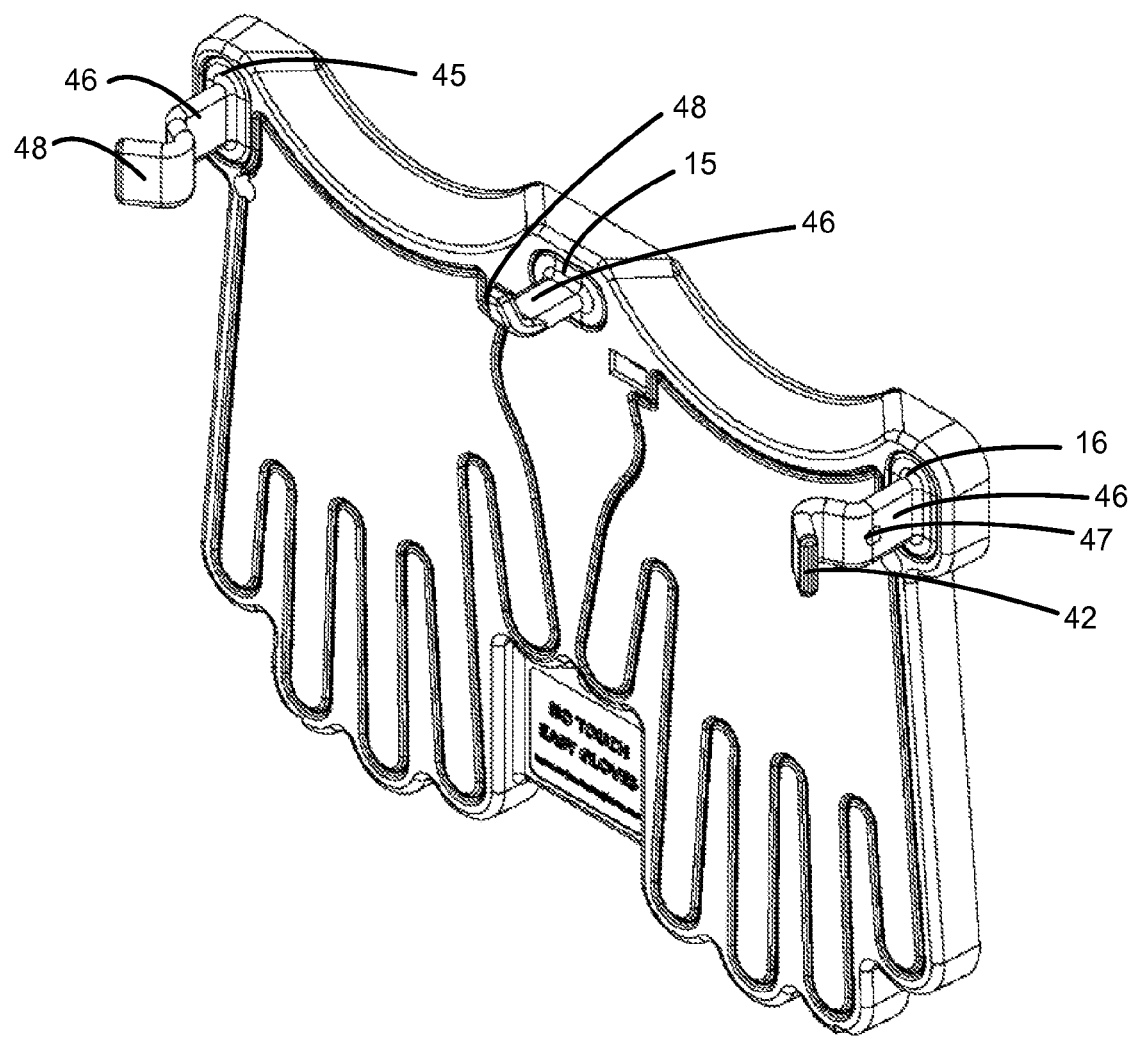
FIG. 7C illustrates a perspective view of a side-by-side glove dispenser and glove hangers, in accordance with various embodiments.
Figure 7D:
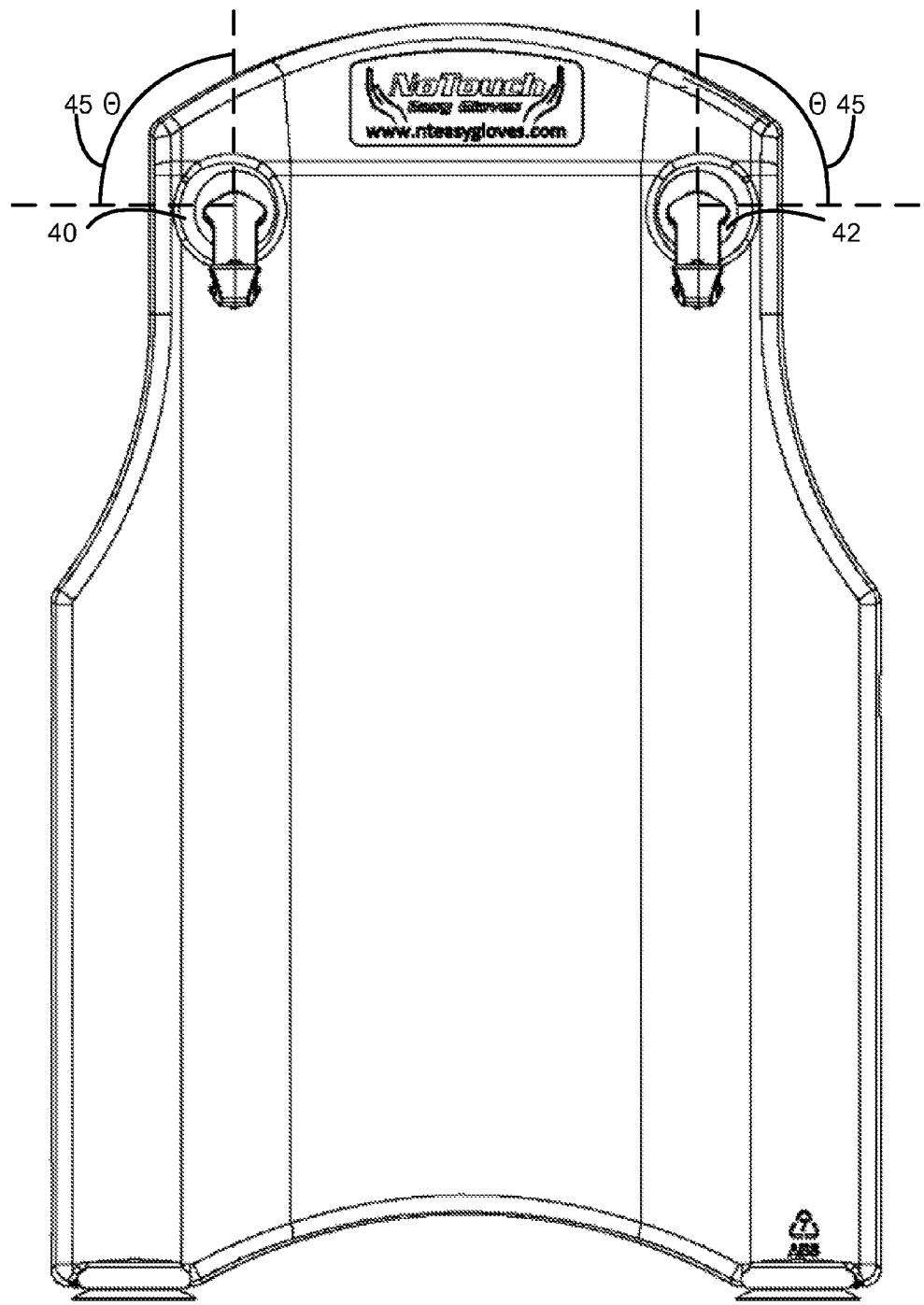
FIG. 7D illustrates a front view of a glove dispenser with glove hangers having a widened retention portion, in accordance with various embodiments.
Figure 7E:
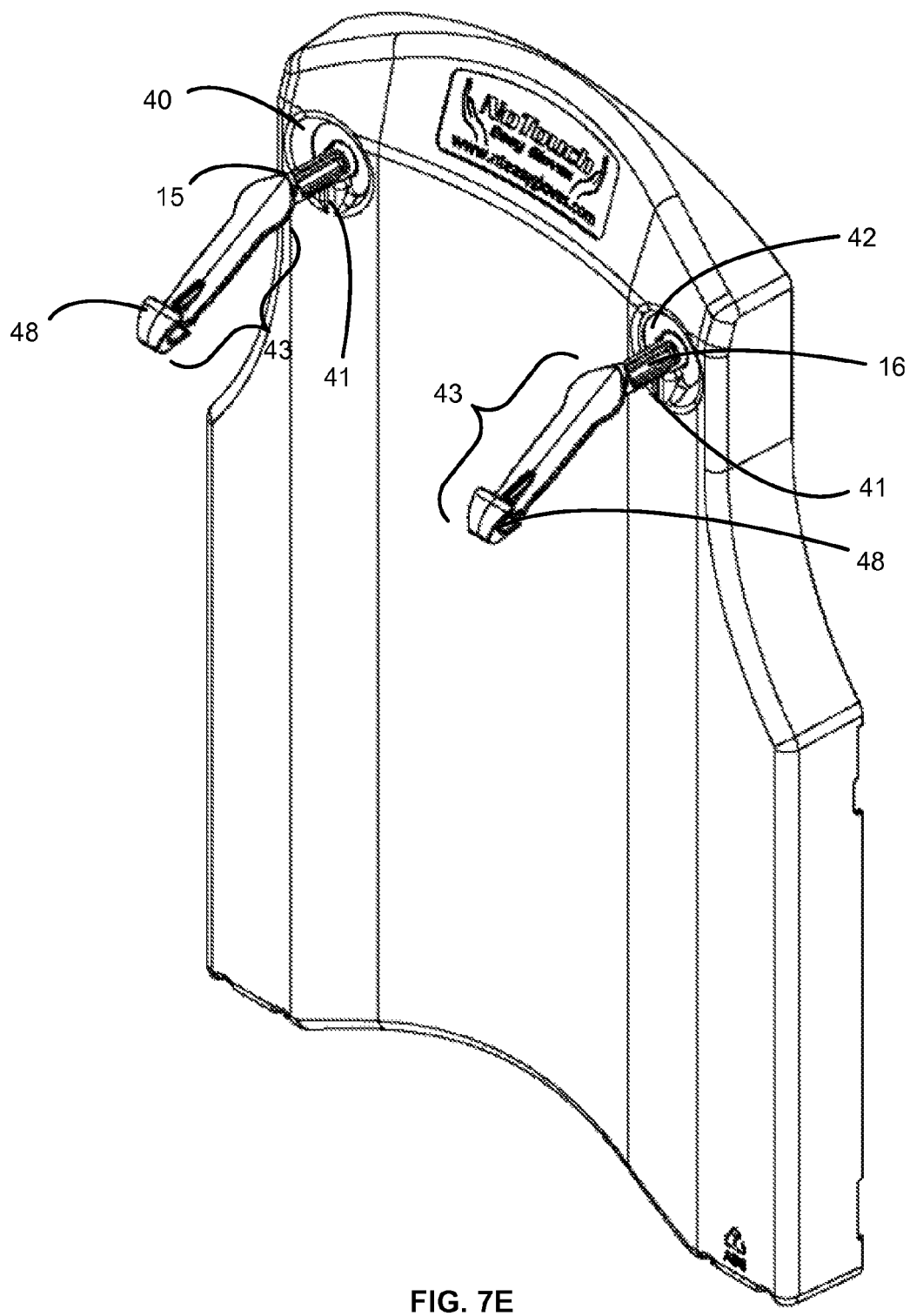
FIG. 7E illustrates a close-up perspective view of a glove dispenser and glove hangers having a widened retention portion, in accordance with various embodiments.

With reference to FIGS. 7A-B and 7D-E, in various embodiments, the first glove hanger aperture 40 may comprise a stop tab 41. Similarly, the second glove hanger aperture 42 may also comprise a stop tab 41. The stop tab 41 may be designed to resist motion of the hanger shaft 46 in the direction of the stop tab 41. The stop tab 41 may be any structure by which movement of a hanger shaft 46 extending from the aperture may be constrained. For example, the stop tab 41 may comprise a boss extending from the circumference of the aperture toward the center of the aperture. The boss may be located at the negative most point of the aperture with respect to the Y-axis. Thus, the boss may be said to be located at the bottom of the aperture. The boss may be unitary with the main body 14 as illustrated in FIG. 5A-C, or may be glued, sonically welded, or otherwise fixed in position. The boss may comprise a separate piece of material, for example, an insert configured to be placed in the aperture or may comprise a piece unitary with the main body 14 as illustrated in FIGS. 7B and 7E.

With reference to FIGS. 5A, 6A-9, the first glove hanger 15 and the second glove hanger 16 each may comprise a flexible base 44, a hanger shaft 46, and an end hook 48. The flexible base 44 may be positioned within the first glove hanger aperture 40 of the main body 14. The hanger shaft 46 may be inserted through the flexible base 44 and may extend outward in an X-axis direction. Further, the end hook 48 may comprise a bent portion of the hanger shaft 46 disposed at a distal end of the hanger shaft 46 with respect to the main body 14. A proximate end of the hanger shaft 46, with respect to the main body 14, may be disposed within the flexible base 44. In this manner, the hanger shaft 46 may be retained securely in connection to the main body 14 via the flexible base 44 inserted within the first glove hanger aperture 40 and/or the second glove hanger aperture 42. However, the flexible base 44 may also be flexible so that the hanger shaft 46 is movable in response to external forces exerted on the hanger shaft 46, for example, by the user's hand. In various embodiments, the flexible base 44 permits the hanger shaft 46 to translate in the Y and Z directions, but not in the X direction.

With reference to FIG. 5B, the first glove hanger 15 and the second glove hanger 16 each may comprise a hanger shaft 46, and an end hook 48. Thus, in various embodiments, the flexible base is omitted. The hanger shaft 46 may be inserted into the main body 14, and may extend outward in an X-axis direction. Further, the end hook 48 may comprise a bent portion of the hanger shaft 46 disposed at a distal end of the hanger shaft 46 with respect to the main body 14. A proximate end of the hanger shaft 46, with respect to the main body 14, may be disposed within the main body 14, and/or may abut against a face of the main body 14 where it is secured by welding, gluing, bonding, or any other method. In this manner, the hanger shaft 46 may be retained securely in connection to the main body 14.

Figure 8A:
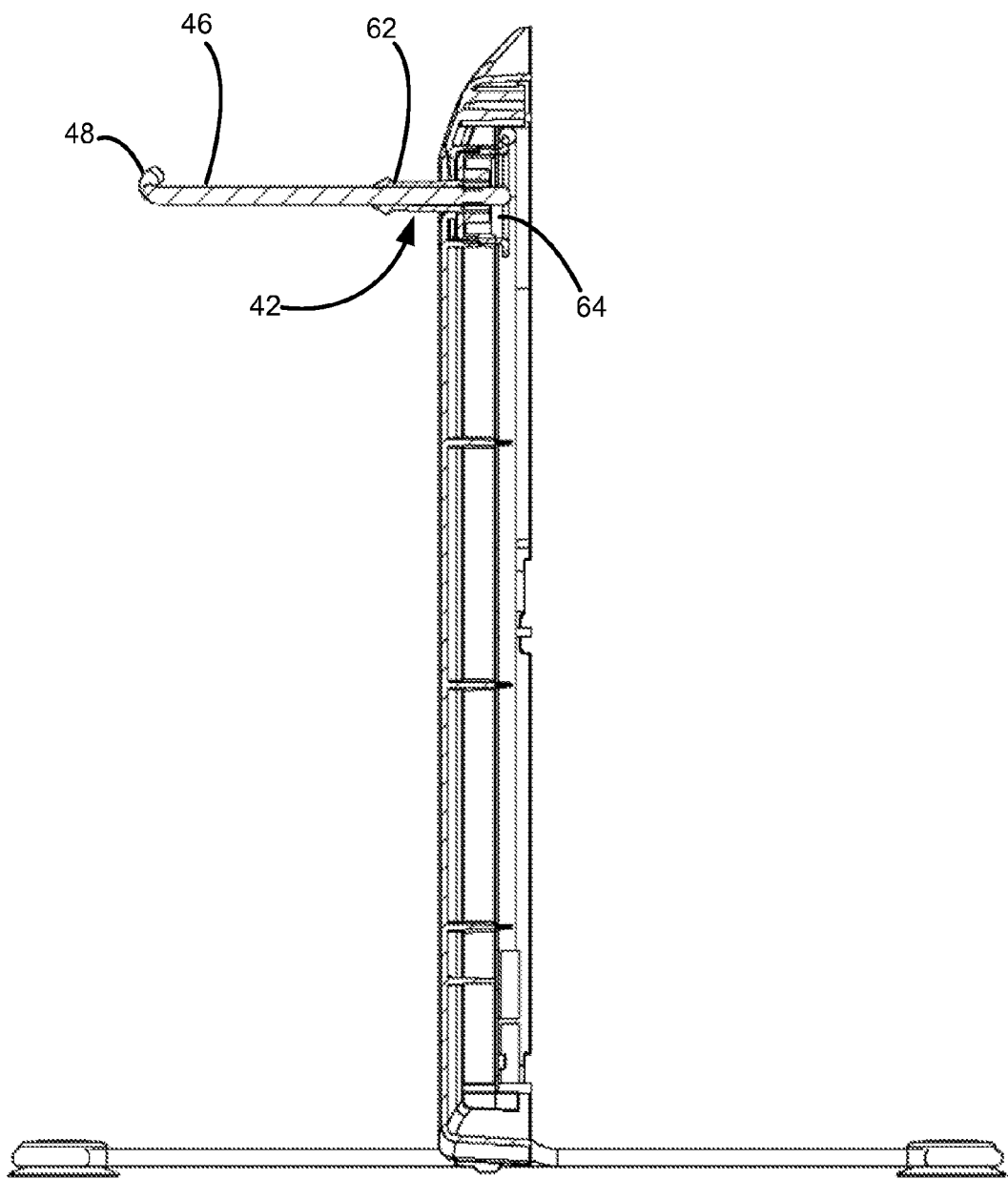
FIG. 8A illustrates a side view of a glove dispenser and glove hangers, in accordance with various embodiments.

In various embodiments and with specific reference to FIG. 8A, the flexible base 44 may comprise a sleeve 62 and a shock absorber 64. With specific reference to FIG. 8C, the flexible base 44 may comprise a shock absorber 64, but omit a sleeve 62 (compare FIG. 8A). The shock absorber 64 may comprise a disc made from a flexible material, for example, rubber. Alternatively, the shock absorber 64 may comprise any shape adapted to fit in the aperture comprising the first glove hanger 15 and/or the second glove hanger 16. The shock absorber 64 may comprise any material suitable to retain the hanger shaft 46, yet permit flexibility. The sleeve 62 may comprise a hollow cylinder extending axially from the shock absorber 64, for example, at its center and extending in the positive X direction. The sleeve 62 may comprise any element configured so that the hanger shaft 46 may extend through the sleeve 62, terminating inside the shock absorber 64. Thus, the flexible base 44 may permit movement of the hanger shaft 46 as discussed herein in response to flexing of the shock absorber 64, yet may prevent the hanger shaft 46 from translating in the X direction via the frictional interaction between the sleeve 62 and the hanger shaft 46.

Figure 8B:
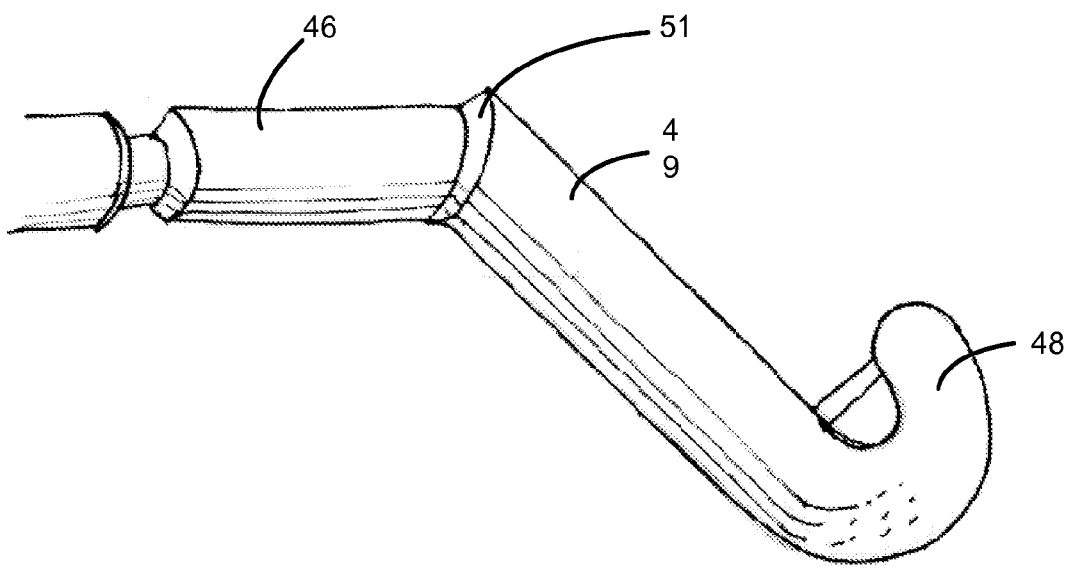
FIG. 8B illustrates a side view of a glove hanger, in accordance with various embodiments.
Figure 8C:
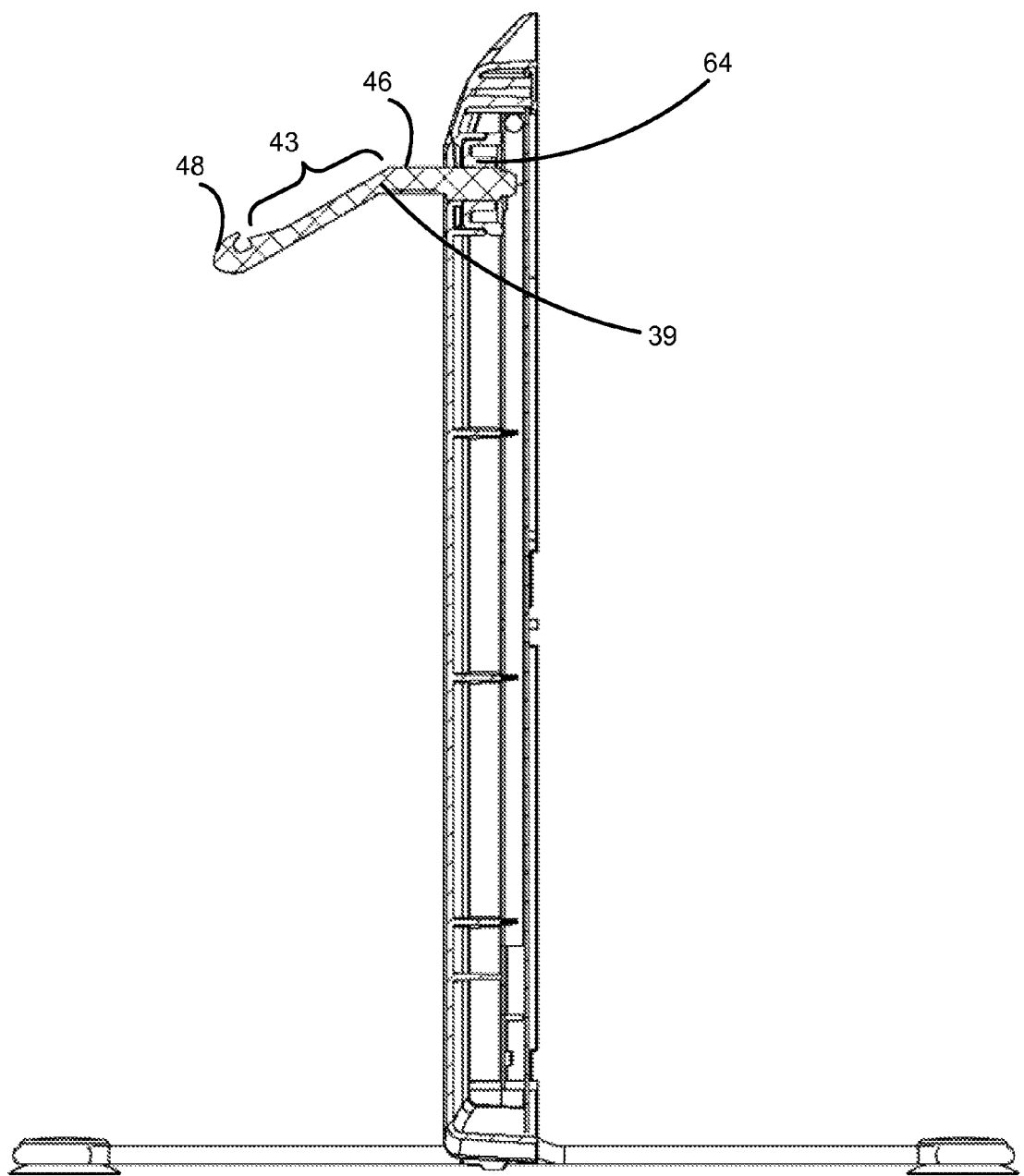
FIG. 8C illustrates a side view of a glove hanger having a widened retention portion, in accordance with various embodiments.

In various embodiments and with specific reference to FIGS. 8B and 8C, the hanger shaft 46 may be bent or otherwise configured to facilitate feeding or dispensing of gloves. For example, a hanger shaft 46 may bend downwardly in order to facilitate gravitational feeding of gloves as the gloves are pulled from the hanger. Moreover, the bend of the shaft may cause a glove that is being dispensed to open so that a user's hand is more easily insertable. Furthermore, because of the bend in the hanger shaft 46, the user is permitted significant latitude in how the user tugs on the glove when dispensing the glove. For instance, the user may pull downward or pull away from the dispenser or may pull in a variety of directions. Because the hanger shaft is bent, a tug in a variety of directions causes a force having a vector component substantially perpendicular to the main body 14. In this manner, the bend in the hanger shaft 46 allows the glove to be torn away and the next glove staged in response to a variety of different tugs in different directions, by the user.

Moreover, the hanger shaft 46 may further comprise an upper retainer 51. The upper retainer 51 may comprise an abrupt change in the diameter of the hanger shaft 46 whereby stored gloves may be prevented from gravity feeding until a force is exerted on them sufficient to translate them past this abrupt change in diameter of the hanger shaft 46, for example by a user's hand. The hanger shaft 46 may further comprise a shaft sleeve 49. Upper retainer 51 may be integrally formed with shaft sleeve 49 and may be an edge of the shaft sleeve 49. In this manner, the abrupt change in diameter of the hanger shaft 46 continues from the upper retainer 51 to the end hook 48. As a result, the increased diameter may ameliorate unwanted movement of gloves by increasing the friction between the glove and the portion of the hanger shaft 46 covered by the shaft sleeve 49. In other embodiments, no shaft sleeve 49 is present, for example, in embodiments wherein the hanger shaft 46 is formed from stamped sheet metal, or in embodiments according to FIG. 8C.

With reference to FIG. 8C, the hanger shaft 46 may comprise a widened retention portion 43. The widened retention portion 43 may comprise a gradual change in the diameter of the hanger shaft 46 and may comprise a flattening of the shaft or otherwise comprise a change in the cross-sectional profile of the shaft. The widened retention portion 43 may be disposed between the shaft angle 39 and the end hook 48. In this manner, stored gloves may be prevented from gravity feeding until a force is exerted on them sufficient to translate them past this change in shape and/or diameter of the hanger shaft 46, for example by a user's hand. As a result, the change in shape and/or diameter may ameliorate unwanted movement of gloves by increasing the friction between the glove and the widened retention portion 43 of the hanger shaft 46. Moreover, when multiple gloves 1 are suspended from the hanger shaft 46, such as when an entire package of gloves 1 is suspended, the bulk of the multiple gloves may cause them to expand as a group over the widened retention portion 43. The distribution of the gloves may be enhanced by the gradual change in the cross-sectional profile of the shaft along the length of the widened retention portion 43.

As briefly mentioned above, the hanger shaft 46 may comprise a shaft angle 39. A shaft angle 39 may comprise a bend in the hanger shaft 46. For example, a hanger shaft 46 may extend away from the main body 14 substantially perpendicular to a face of the main body 14. At the shaft angle 39, the hanger shaft 46 may transition to also extend downwardly and away from the face of the main body 14.

Returning focus to the glove hanger and referencing FIGS. 5A-9, the first glove hanger 15 and the second glove hanger 16 may each comprise an end hook 48 disposed at the distal end of the hanger shaft 46. The end hook 48 may comprise a C-shape bent portion of the hanger shaft 46. Alternatively, the end hook 48 may comprise a U-shaped bent portion of the hanger shaft 46. Furthermore, the end hook 48 may comprise an upturned bent portion of the hanger shaft 46. In various embodiments, the end hook 48 may further comprise a retention bump 47 (FIG. 7C) extending from a surface of the hanger shaft 46 and enhancing frictional engagement between the hanger shaft 46 and an item to be hanged from the hanger shaft 46, for example, a glove. In various embodiments, the end hook is shaped to resemble a triangle so that the end hook 48 is wider at the outermost edge than where it unites with the hanger shaft 46. In this manner, the frictional engagement may be increased between the hanger shaft 46 and an item to be hanged from the hanger shaft 46, for example, a glove. As a result, the item to be hanged from the hanger shaft 46 may be prevented from inadvertently falling off of the end hook 48, for example, in response to a wind or inadvertent brushing by a person. The end hook 48 may comprise a thickened portion of the hanger shaft 46, or may comprise any shape configured to provide increased frictional engagement between the hanger shaft 46 and an item to be hanged from the hanger shaft 46, for example, a glove.

Moreover, with reference to FIGS. 7A and 7D, the end hook 48 may be set at a selected angle, referred to herein as a hanger angle 45, which may be set directly upward, outward, or inward relative to the center of the main body 14. The hanger angle 45 may comprise an angle between the Z-axis and a line extending through and parallel to the end hook 48 of the hanger shaft 46. For example, the hanger shaft 46 may be positioned so that the end hook 48 extends coincident with a line disposed at the hanger angle 45 above the X-axis. In this manner, the end hook 48 may extend upward and outward (e.g., in the Y and Z direction) from the center of the main body 14.

In various embodiments, the first glove hanger 15 has a hanger angle 45 and the second glove hanger 16 also has a separate hanger angle 45. In various embodiments, each hanger angle 45 may comprise an angle having the same angular magnitude. The first glove hanger 15 may have an hanger angle 45 comprising an angle between the Z-axis and a line extending through the end hook 48 of the hanger shaft 46 wherein the line is oriented above (in the positive Y direction) the Z-axis at the angle. Similarly, the second glove hanger 16 may have a hanger angle 45 comprising an angle between the Z-axis and a line extending through the end hook 48 of the hanger shaft 46 wherein the line is oriented above (in the positive Y direction) the Z-axis at the angle. In this manner, each end hook 48 may point upward and outward from the center of the main body 14. The hanger angle 45 may comprise a 45 degree angle (FIG. 7A), or a 90 degree angle (FIG. 7D) or any desired angle.

Now, having discussed various aspects of the glove dispenser 2, the main body 14 may be configured in various ways to permit the glove dispenser 2 to be mounted and oriented differently, or for multiple glove dispensers 2 to be joined together. For example, in various embodiments and with reference to FIGS. 10-14, the glove dispenser 2 may be configured to hang from a surface, such as a wall (illustrated in FIG. 10), the glove dispenser 2 may be configured to be joined together back-to-back with an opposite facing a glove dispenser 2 (illustrated in FIG. 11A-B), the glove dispenser 2 may be singular and have legs (illustrated in FIG. 12), or the glove dispenser 2 may be configured to be joined side to side with a similarly facing glove dispenser 2 (illustrated in FIGS. 13A-B and 14A-B). As one may appreciate, the glove dispenser 2 may be reconfigurable to be mounted or oriented in a variety of ways and aspects of various embodiments and configurations may be combined. For example, a kit of parts may be provided to permit the glove dispenser 2 to be reconfigured variously.

Figure 10:
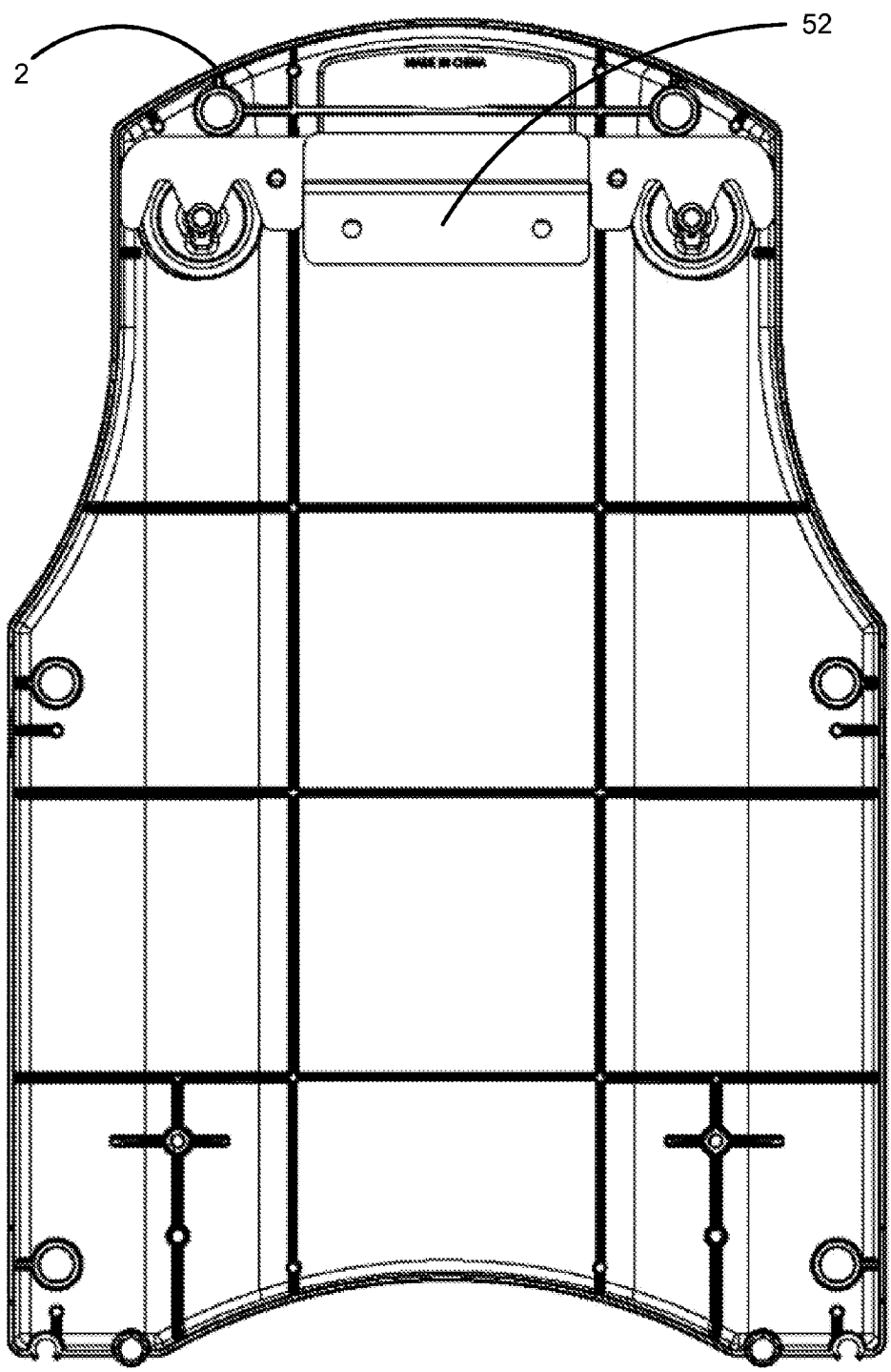
FIG. 10 illustrates a back view of a hanging glove dispenser, in accordance with various embodiments.

For example, in various embodiments, with reference to FIG. 10, the main body 14 may comprise a hanging bracket 52. The hanging bracket 52 may be disposed in the Y-Z plane along a face of the main body 14, for example, along the back side of main body 14 opposite the glove retention member 12. In various embodiments, the hanging bracket 52 is a metal tab, although the hanging bracket 52 may be any element adapted to enable the main body 14 to be attached to a surface, for example, screwed, nailed, adhered, suctioned, or otherwise fastened to a wall.

Figure 11A:
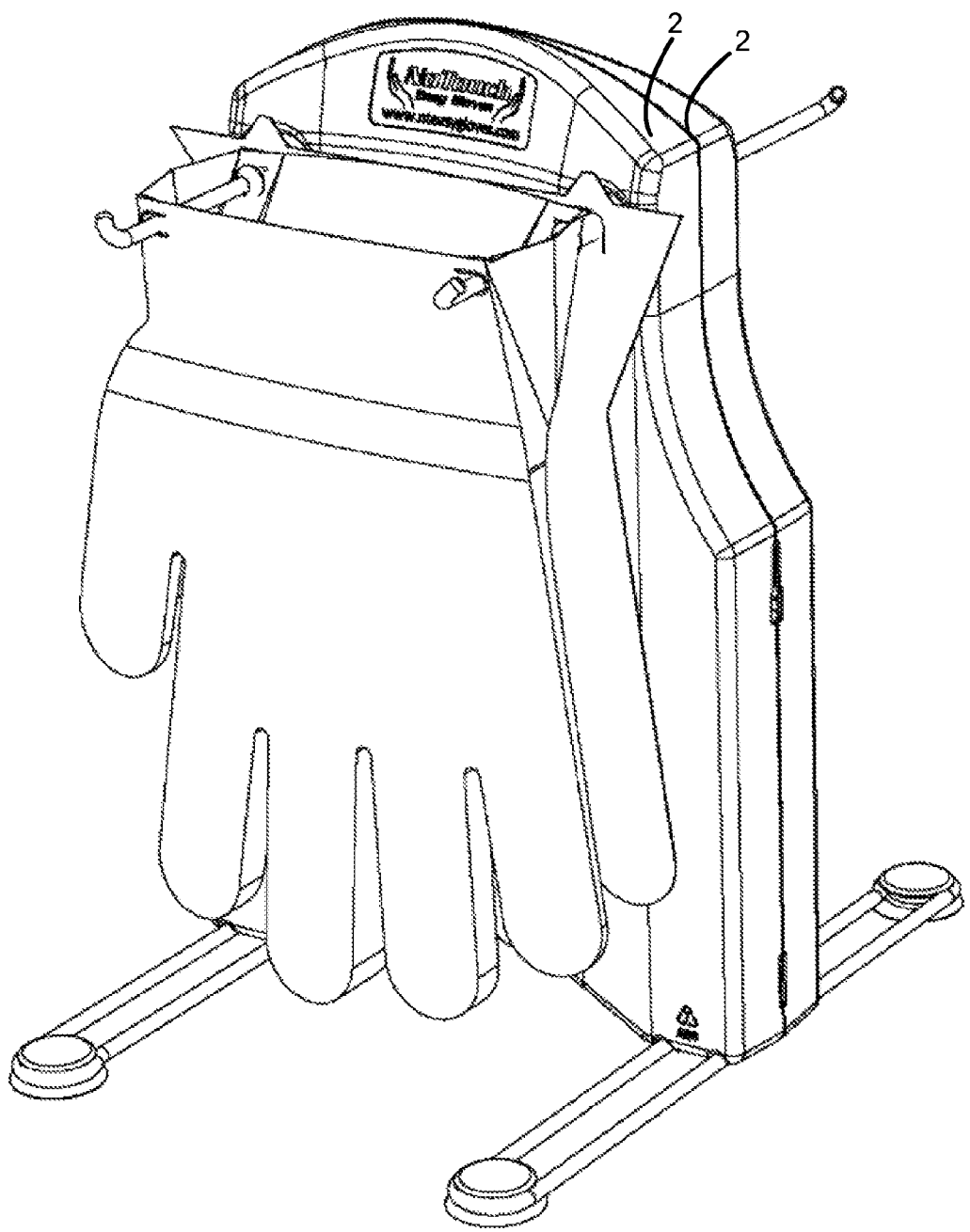
FIG. 11A illustrates a perspective view of a back-to-back glove dispenser stand, in accordance with various embodiments.
Figure 11B:
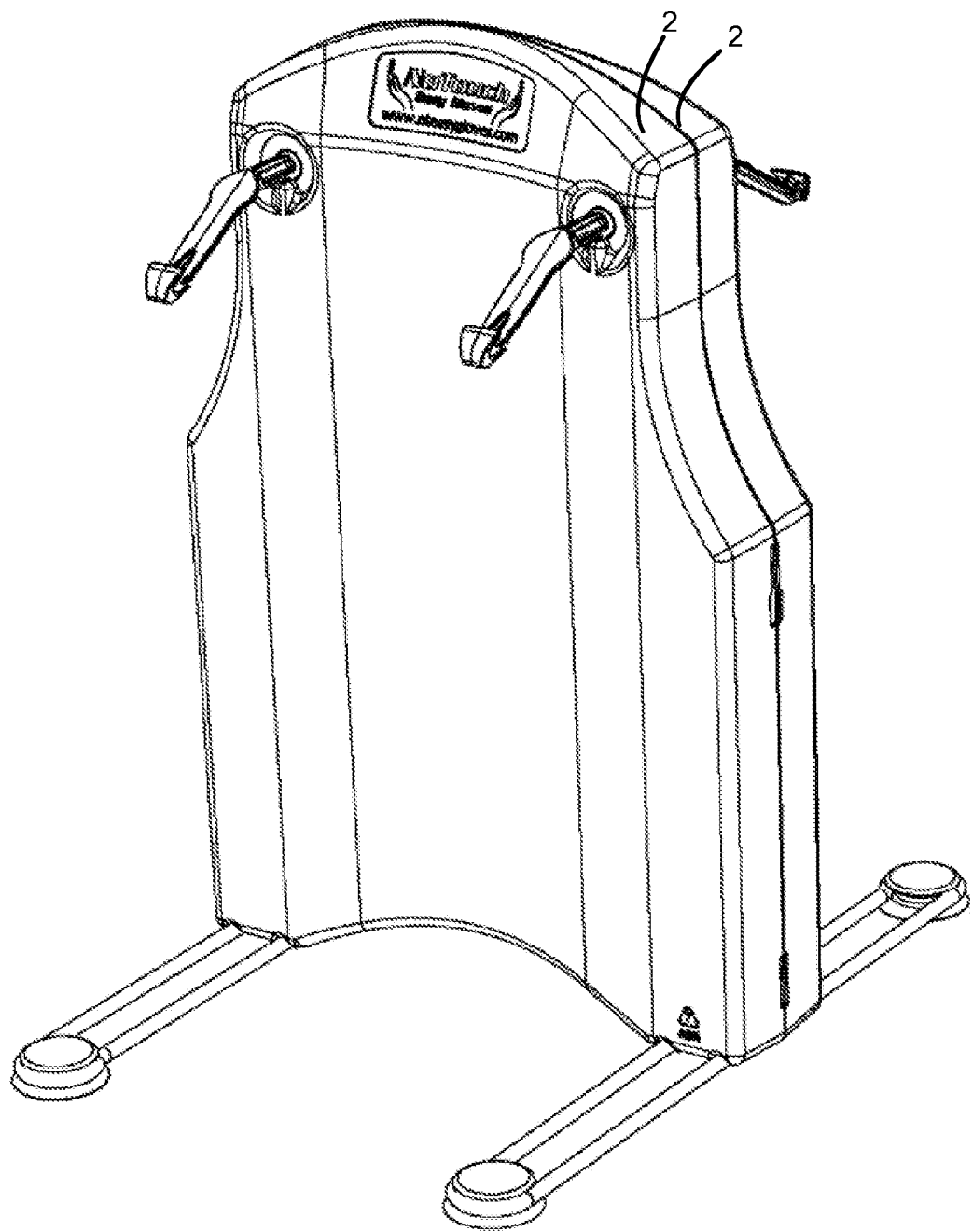
FIG. 11B illustrates a perspective view of a back-to-back glove dispenser stand with glove hangers having a widened retention portion, in accordance with various embodiments.
Figure 12:
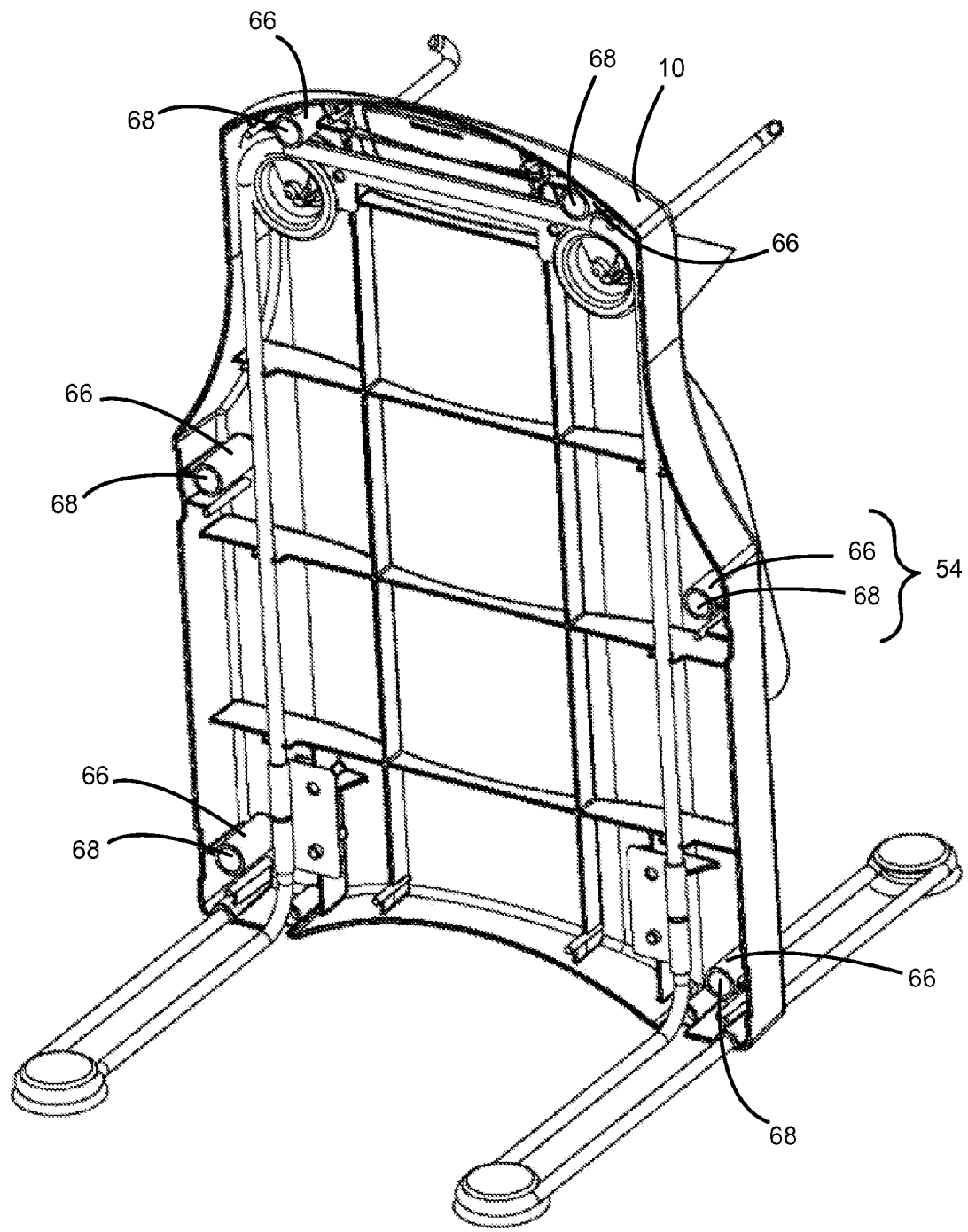
FIG. 12 illustrates a perspective view of the back of a glove dispenser, in accordance with various embodiments.
Figure 13A:
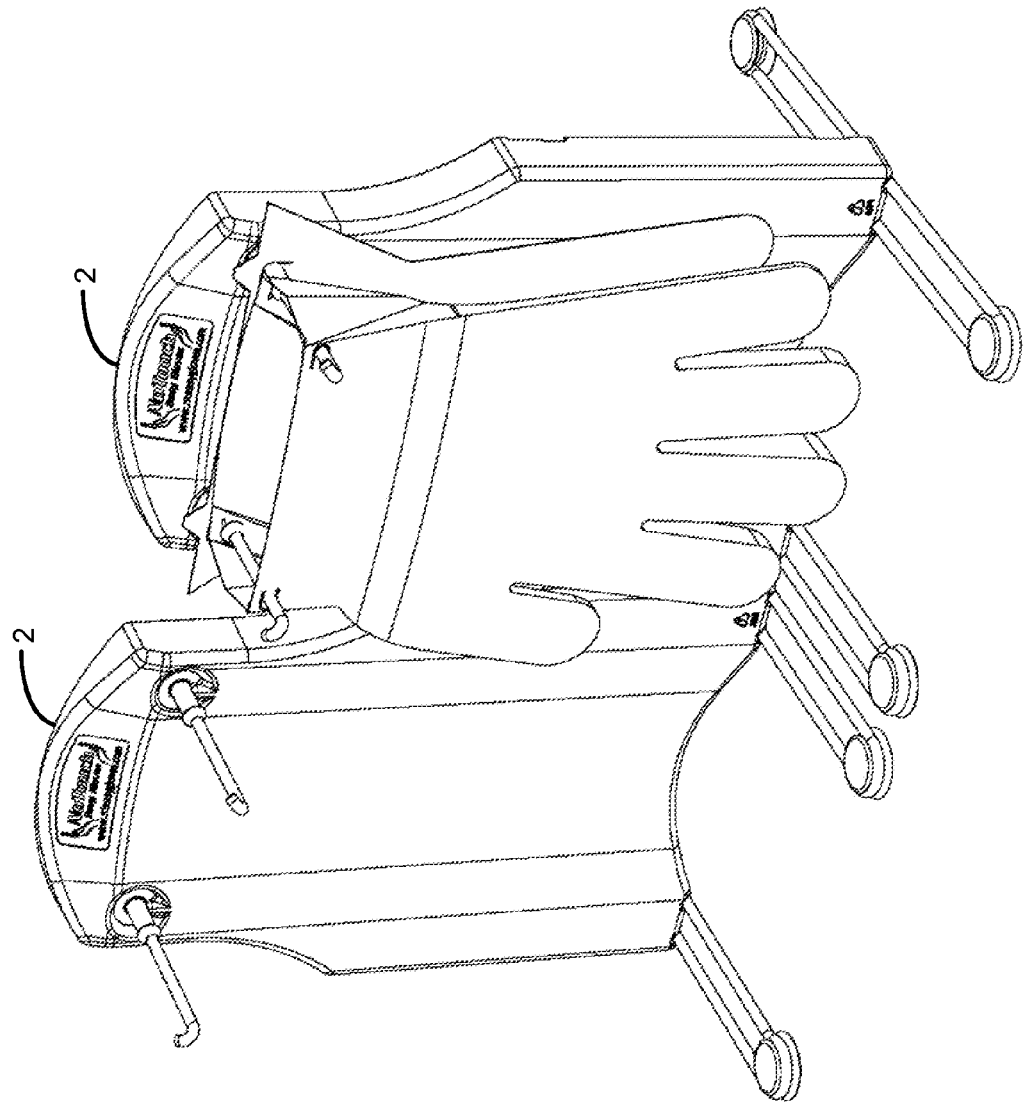
FIG. 13A illustrates a perspective view of the front of a side-by-side glove dispenser, in accordance with various embodiments.
Figure 13B:
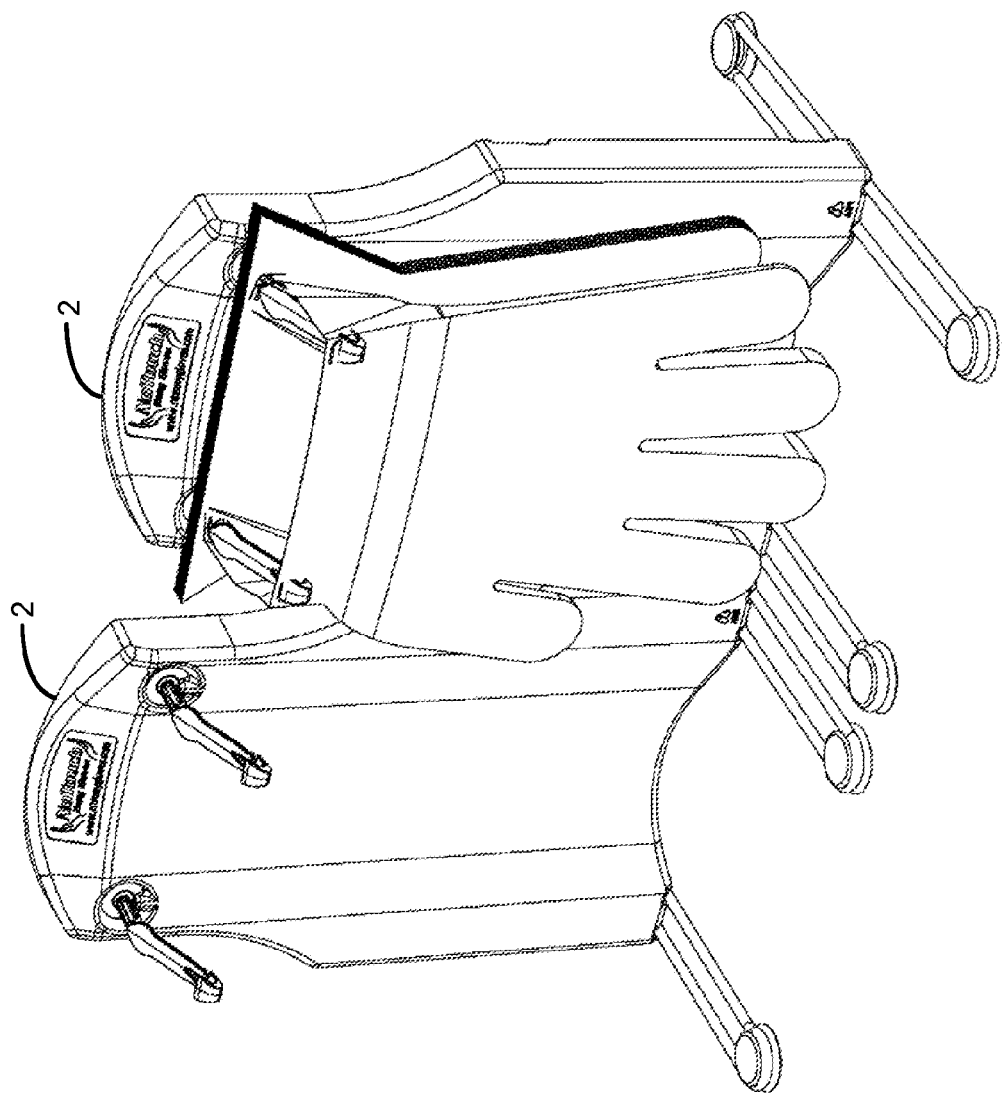
FIG. 13B illustrates a perspective view of the front of a side-by-side glove dispenser with glove hangers having a widened retention portion, in accordance with various embodiments.
Figure 14A:
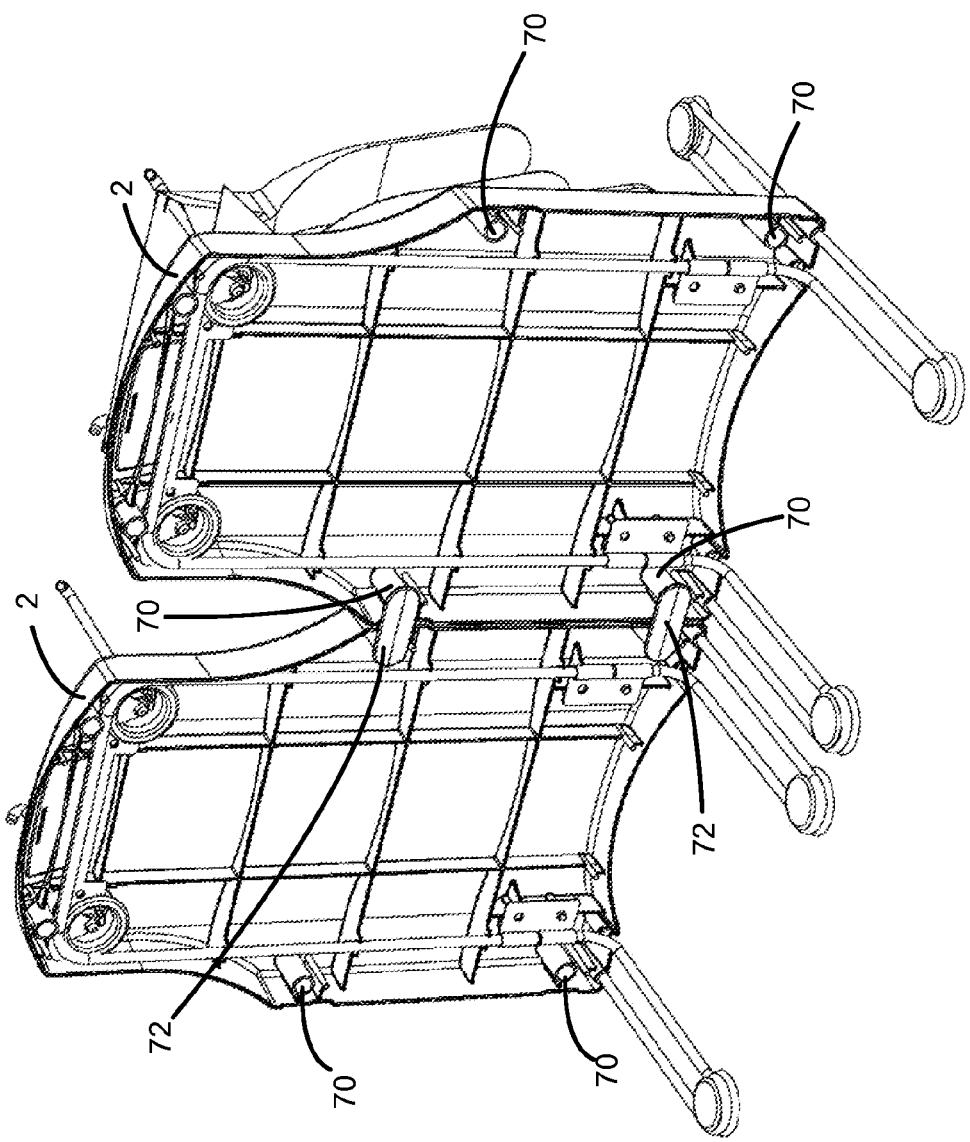
FIG. 14A illustrates a perspective view of the back of a side-by-side glove dispenser, in accordance with various embodiments.
Figure 14B:
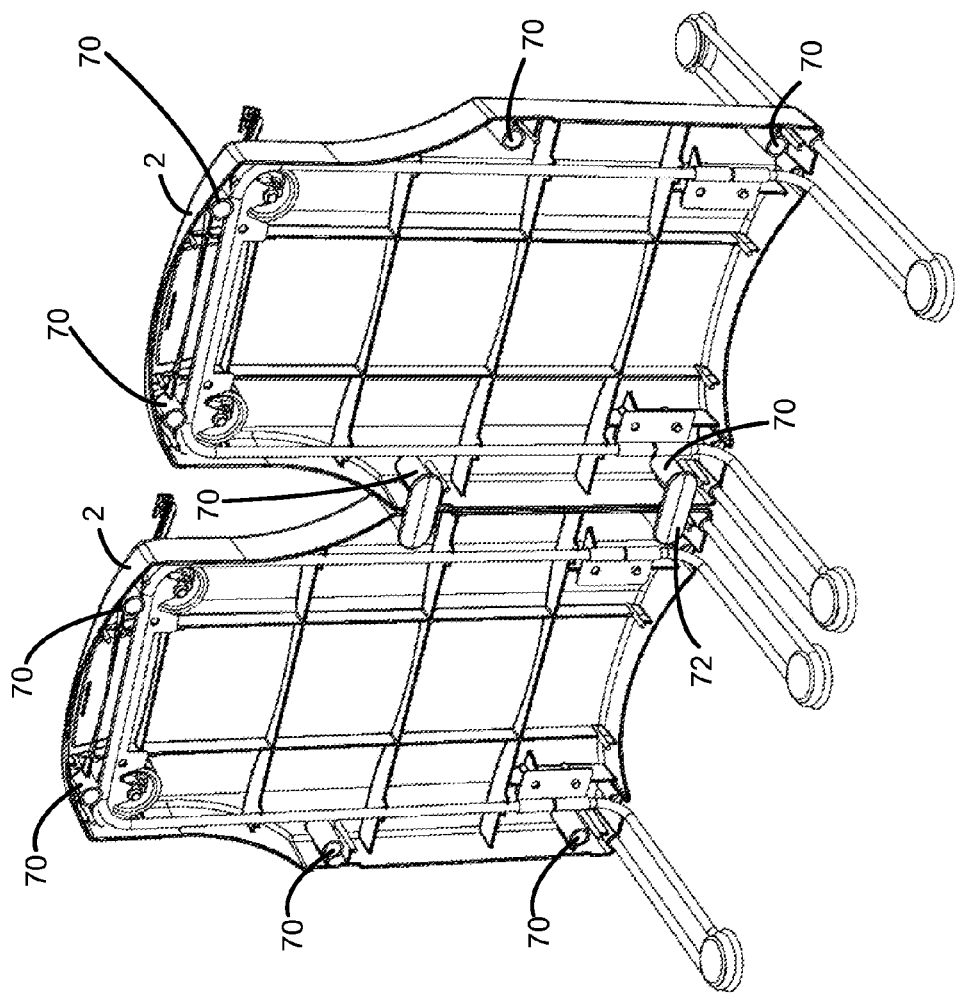
FIG. 14B illustrates a perspective view of the back of a side-by-side glove dispenser with glove hangers having a widened retention portion, in accordance with various embodiments.

To facilitate the back-to-back variation, in various embodiments, with reference to FIGS. 11A, 11B, and 12, the main body 14 may comprise a back-to-back stand attachment member 54. For example, the glove dispenser 2 may have a member that permits the glove dispenser 2 to be joined with another glove dispenser 2 wherein the glove retention member 12 of each glove dispenser 2 is oriented in an opposite direction. In this manner, the glove dispensers 2 may be said to be back to back and a user may put gloves on both hands simultaneously.

As shown in the backside view of FIG. 12, in various embodiments, a back-to-back stand attachment member 54 comprises an aperture 66 and a back-to-back connector 68. The aperture 66 may be positioned on the backside of the main body 14. In various embodiments, more than one aperture 66 is positioned around a perimeter of the main body 14. A back-to-back connector 68 may comprise a plug adapted to fit in the aperture 66, being retained by friction to the aperture, and extend therefrom. For example, the back-to-back connector 68 may be a cylinder. In various embodiments, a second glove dispenser 2 also having similarly spaced apertures 66 may be positioned so that the back-to-back connectors 68 align with corresponding similarly spaced apertures 66. Thus, the two glove dispensers 2 may be joined together by the insertion of back-to-back connectors 68 into the apertures 66 of both the glove dispensers 2.

To facilitate the side-by-side variation, with reference to FIGS. 13A-B and 14A-B, in various embodiments, a side-by-side stand attachment member 56 comprises an aperture 70 and a side-by-side tab 72. The aperture 70 may be positioned on the backside of the main body 14. In various embodiments, more than one aperture 70 is positioned around a perimeter of the main body 14. In various embodiments, the locations of aperture 70 may be the same as the locations of aperture 66. The side-by-side tab 72 may comprise a pair of plugs (a first plug and a second plug) joined together and each adapted to fit in an aperture 70, being retained by friction to the aperture, and extend therefrom. For example, the side-by-side tab 72 may comprise a planar member comprising a face with two cylindrical plugs projecting outward in the same direction. One such plug may be inserted in an aperture 70 of a first glove dispenser 2 and the other plug may be inserted into an aperture 70 of a second glove dispenser 2. Thus, in various embodiments, the second glove dispenser 2 also having similarly spaced apertures 70 may be positioned so that the side-by-side tabs 72 align with the corresponding similarly spaced apertures 70. Thus, the two glove dispensers 2 may be joined together by the insertion of side-by-side tabs 72 into the apertures 70 of both glove dispensers 2. The glove dispensers 2 may be positioned adjacently with the face of each glove dispenser 2 facing in the same direction. In this manner, the glove dispensers 2 may be positioned so that a user may put gloves on both hands simultaneously.

Now, having described various components of various exemplary embodiments of the glove dispenser 2, the glove dispenser 2 may be manufactured from various materials. In one exemplary embodiment, the glove dispenser 2 may comprise metal, plastic, or a combination thereof. For example, the glove dispenser 2 may comprise metal, such as aluminum. Alternatively, the glove dispenser 2 may comprise metal, such as titanium, steel, or stainless steel, though it may alternatively comprise numerous other materials configured to provide support, such as, for example, fiberglass composite, ceramic, ceramic matrix composite, plastics, polymers, alloys, austenitic nickel-chromium-based alloys, glass, binder, epoxy, polyester, acrylic or any material or combination of materials having a desired strength, stiffness, density, weight, or flexibility sufficient to maintain resiliency during use. In various embodiments, various portions of the glove dispenser 2 as disclosed herein are made of different materials or combinations of materials, and/or may comprise coatings.

In various embodiments, the glove dispenser 2 may comprise multiple materials, or any material configuration suitable to enhance or reinforce the resiliency and/or support of the glove dispenser 2 when subjected to wear in an operating environment or to satisfy other desired weight, size, cost, chemical, physical, or biological properties, for example non-reactivity, light weight, load capacity, and heat tolerance. For example, various components may comprise metal while other components may comprise plastics and/or rubber.

In various embodiments, while the glove dispensers 2 described herein have been described in the context of glove support; however, one will appreciate in light of the present disclosure, that the apparatuses described herein, for example, the glove dispensers 2 may be used in connection with various other applications, for example in connection with various glove applications and dispensing applications.

In various embodiments, the disposable gloves 1 described herein may be packaged for shipping. For example, with reference to FIGS. 15A-B, a set of multiple disposable gloves 1 may be packaged within a sanitary sealed film glove package 1500. The sanitary sealed film glove package 1500 may comprise a forward face 1501 and an aft face 1504. The forward face 1501 may comprise a film that is aligned to the outermost glove in the set and the aft face 1504 may comprise a film that is aligned to the innermost glove in the set. With momentary reference to FIG. 3B, the gloves 1 in the set may each comprise tear points 8, as previously discussed. At least one of the forward face 1501 and the aft face 1504 may comprise a metallic ink printed on a position that is aligned with a tear point 8 when the gloves are packaged within the sanitary sealed film glove package 1500. The forward face 1501 and the aft face 1504 may be pressed together so that they contact at the tear point 8, for example, through an aperture of the tear point 8. The sanitary sealed film glove package 1500 and gloves 1 may be exposed to RF energy, for example, during RF welding, so that the metallic ink heats and causes the forward face 1501 and the aft face 1504 to weld and/or melt together through the tear point 8. In this manner, the sanitary sealed film glove package 1500 may be secured around the gloves 1 and may be retained in position relative to them.

The sanitary sealed film glove package 1500 may further comprise hanger slits 1503 comprising cuts, perforations, and/or apertures disposed within the sanitary sealed film glove package 1500 and aligned to the interconnection points 4 of the gloves 1. Thus, the entire package may hang on the glove dispenser 2. The sanitary sealed film glove package 1500 may further comprise grip points 1502 where the user may grasp the sanitary sealed film glove package 1500 and compress the sanitary sealed film glove package 1500 between one's fingers, without grasping the gloves 1 disposed inside the sanitary sealed film glove package 1500. In various embodiments, the grip points 1502 comprise the lower corners of the package nearest the fingers of the gloves 1. The package may be torn away by pulling the package downward after grasping a grip point 1502. A strategic perforation may be disposed along the upper edge of the package, or alternatively, the upper edge of the package may be open. The package may tear along this perforation, if present, so that the package may be torn away.

The gloves 1 and/or sanitary sealed film glove package 1500 may be manufactured from various materials. In one exemplary embodiment, the gloves 1 and/or sanitary sealed film glove package 1500 may comprise plastics, silicones, latex, or a combination thereof. For example, the gloves 1 and/or sanitary sealed film glove package 1500 may comprise thermoplastic aliphatic polyester, such as polylactide (PLA), or may comprise other thermoplastics, such as acrylonitrile butadiene styrene (ABS) plastic, or may comprise any plastic. The gloves 1 and or sanitary sealed film glove package 1500 may comprise a PLA material made from corn-based resin, or starch-based resin, or resin derived from petroleum or non-petroleum sources. The gloves 1 and/or sanitary sealed film glove package 1500 may comprise polyethylene, nitrile, vinyl, latex, and/or any other suitable material. The gloves 1 and/or sanitary sealed film glove package 1500 may comprise numerous other materials configured to provide support, such as, for example, fiberglass composite, ceramic, ceramic matrix composite, plastics, polymers, glass, binder, epoxy, polyester, acrylic or any material or combination of materials having a desired strength, stiffness, density, weight, or flexibility sufficient to maintain resiliency during use. In various embodiments, various portions of the gloves 1 and/or sanitary sealed film glove package 1500 as disclosed herein are made of different materials or combinations of materials, and/or may comprise coatings.

In various embodiments, the gloves 1 and or sanitary sealed film glove package 1500 may comprise multiple materials, or any material configuration suitable to enhance or reinforce the resiliency and/or support of the gloves 1 and/or sanitary sealed film glove package 1500 when subjected to wear in an operating environment or to satisfy other desired weight, size, cost, chemical, physical, or biological properties, for example nonreactivity, light weight, load capacity, and heat tolerance. For example, various components may comprise plastic while other components may comprise rubber.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A disposable glove comprising:
   an opening for hand entry having a first opening edge on a forward side of the disposable glove and a second opening edge on an aft side of the disposable glove;
   a first interconnection point located near the first opening edge, wherein the first interconnection point attaches the disposable glove to a first adjacent disposable glove; and a second interconnection point located near the second opening edge, wherein the second interconnection point attaches the disposable glove to a second adjacent disposable glove, wherein the disposable glove is positioned between the first adjacent disposable glove and the second adjacent disposable glove; and two tear points passing through both the forward side and the aft side of the disposable glove.

2. The disposable glove of claim 1, further comprising at least one gusset configured to increase a size of the opening for hand entry.

3. The disposable glove of claim 1, further comprising a plurality of tack points along an inside perimeter of the disposable glove.

4. The disposable glove of claim 1, wherein the first interconnection point and the second interconnection point attaches via heat sealing, an adhesive, an interlock tab, or a combination thereof.

5. The disposable glove of claim 1, wherein the disposable glove hangs from a glove dispenser, and wherein the glove dispenser comprises a first glove hanger and a second glove hanger.

6. The disposable glove of claim 5, wherein the first glove hanger and the second glove hanger each pass through a hanger opening in the disposable glove.

7. The disposable glove of claim 6, wherein the hanger opening is formed by cutting a flap into the disposable glove, and wherein the first interconnection point and the second interconnection point are formed by attaching the flap of the hanger opening to the first adjacent disposable glove and the second adjacent disposable glove, respectively.

8. A disposable glove dispensing system comprising:
a pack of disposable gloves, wherein an individual disposable glove of the pack of disposable gloves is interconnected to a first and a second adjacent disposable gloves, the individual disposable glove comprising:
a first opening edge interconnected to the first adjacent disposable glove;
a second opening edge interconnected to the second adjacent disposable glove; and
a glove dispenser comprising a main body connected to a first glove hanger and a second glove hanger, the main body further comprising a first glove hanger aperture and a second glove hanger aperture wherein the first glove hanger comprises a flexible base comprising a shock absorber disposed within the first glove hanger aperture and the second glove hanger comprises a flexible base comprising a shock absorber disposed within the second glove hanger aperture, and
wherein the pack of disposable gloves hang from the first glove hanger and the second glove hanger.

9. The disposable glove dispensing system of claim 8, the glove dispenser further comprising a main body connected to the first glove hanger and the second glove hanger, and further comprising a support member connected to the main body.

10. The disposable glove dispensing system of claim 9, wherein the first glove hanger and the second glove hanger extend outwardly from a face of the main body.

11. The disposable glove dispensing system of claim 9, wherein the support member is removable.

12. The disposable glove dispensing system of claim 9, wherein the support member comprises:
a first forward leg and a second forward leg spaced along a first face of the main body, and
a first aft leg and a second aft leg spaced along a second face of the main body,
wherein the first face of the main body and the second face of the main body comprise parallel opposite faces.

13. The disposable glove dispensing system of claim 9, wherein the main body further comprises a first glove hanger aperture and a second glove hanger aperture, and
wherein the first glove hanger is disposed within the first glove hanger aperture and the second glove hanger is disposed within the second glove hanger aperture.

14. The disposable glove dispensing system of claim 13, wherein the first glove hanger aperture comprises a first stop tab comprising a boss extending from a circumference of the first glove hanger aperture toward a center of the first glove hanger aperture whereby movement of the first glove hanger is constrained, and
wherein the second glove hanger aperture comprises a second stop tab comprising a boss extending from a circumference of the second glove hanger aperture toward the center of the second glove hanger aperture whereby movement of the second glove hanger is constrained.

15. The disposable glove dispensing system of claim 14, wherein the first glove hanger is constrained from moving in a downward direction and wherein the second glove hanger is constrained from moving in the downward direction.

16. The disposable glove dispensing system of claim 14, wherein the first glove hanger comprises:
a flexible base comprising:
a shock absorber disposed within the first glove hanger aperture; and
a sleeve comprising a hollow cylinder extending axially from the shock absorber;
wherein a hanger shaft is disposed within the sleeve and extending axially from the shock absorber; and
an end hook comprising a bent portion of the hanger shaft disposed at a distal end of the hanger shaft.

17. The disposable glove dispensing system of claim 16, wherein the hanger shaft comprises a retention bump whereby a first opening edge of a glove may be retained aft of the retention bump and a second opening edge of the glove may be disposed forward of the retention bump.

18. The disposable glove dispensing system of claim 16, wherein the hanger shaft comprises a first retention bump disposed on the hanger shaft and a second retention bump disposed on the hanger shaft axially outward of the first retention bump whereby a first opening edge of a glove may be retained aft of the first retention bump and a second opening edge of the glove may be disposed forward of the second retention bump.

19. The disposable glove dispensing system of claim 14, wherein the first glove hanger comprises:
a flexible base comprising a shock absorber disposed within the first glove hanger aperture;
a hanger shaft disposed within the shock absorber and extending axially from the shock absorber; and
an end hook comprising a bent portion of the hanger shaft disposed at a distal end of the hanger shaft.

20. The disposable glove dispensing system of claim 19, wherein the hanger shaft comprises:
a shaft angle transition comprising a downward bend in the hanger shaft; and
a widened retention portion disposed between the shaft angle transition and the end hook,
wherein a first opening edge of a glove may be retained aft of the widened retention portion and a second opening edge of the glove may be disposed forward of the widened retention portion.

21. The disposable glove dispensing system of claim 9, wherein the main body comprises a back-to-back stand attachment member comprising:
   an aperture positioned on a backside of the main body; and
   a back-to-back tab comprising a plug inserted into the aperture and extending outward from the aperture and adapted to join a second glove dispenser having a similar aperture.

22. The disposable glove dispensing system of claim 9, wherein the main body comprises a side-to-side stand attachment member comprising:
   an aperture positioned on a backside of the main body; and
   a side-to-side tab comprising a planar member comprising a face with a first plug and a second plug projecting outward in the same direction,
   wherein the first plug is positioned in the aperture, and
   wherein the second plug is configured to be positioned in a similar aperture of a second glove dispenser.

23. A method of dispensing a disposable glove comprising:
   opening the disposable glove comprising:
      a first opening edge on a forward side of the disposable glove and configured to be interconnected to a first adjacent disposable glove;
      a second opening edge on an aft side of the disposable glove and interconnected to a second adjacent disposable glove; and
      two tear points passing through both the forward side and the aft side of the disposable glove,
   wherein the disposable glove hangs from a glove dispenser comprising a first glove hanger and a second glove hanger,
   wherein the disposable glove is attached to the second adjacent disposable glove by an interconnection point located near the second opening edge;
   inserting a hand into the disposable glove;
   tearing the interconnection point; and
   removing the disposable glove from the glove dispenser.

24. A disposable glove comprising:
   an opening for hand entry having a first opening edge and a second opening edge;
   a first interconnection point located near the first opening edge and comprising a tab from a punch-out of a hole configured to receive a first glove hanger, wherein the first interconnection point is configured to attach the disposable glove to a first adjacent disposable glove; and
   a second interconnection point located near the second opening edge and comprising a tab from a punch-out of a hole configured to receive a second glove hanger, wherein the second interconnection point is configured to attach the disposable glove to a second adjacent disposable glove, wherein the disposable glove is positioned between the first adjacent disposable glove and the second adjacent disposable glove.

\* \* \* \* \*